US008895608B2

(12) United States Patent
Iadonato et al.

(10) Patent No.: US 8,895,608 B2
(45) Date of Patent: Nov. 25, 2014

(54) SULFONAMIDE ANTI-VIRAL COMPOUNDS

(75) Inventors: Shawn P. Iadonato, Seattle, WA (US); Kristin Bedard, Seattle, WA (US)

(73) Assignee: Kineta, Inc., Seattle, WA (US)

( * ) Notice: Subject to any disclaimer, the term of this patent is extended or adjusted under 35 U.S.C. 154(b) by 30 days.

(21) Appl. No.: 13/642,822

(22) PCT Filed: Apr. 20, 2011

(86) PCT No.: PCT/US2011/033338
§ 371 (c)(1),
(2), (4) Date: Oct. 22, 2012

(87) PCT Pub. No.: WO2011/133729
PCT Pub. Date: Oct. 27, 2011

(65) Prior Publication Data
US 2013/0039945 A1    Feb. 14, 2013

Related U.S. Application Data

(60) Provisional application No. 61/327,571, filed on Apr. 23, 2010.

(51) Int. Cl.
*A61K 31/34* (2006.01)
*C07D 409/12* (2006.01)
*A61K 31/36* (2006.01)
*A61K 31/38* (2006.01)
*C07D 333/34* (2006.01)
*C07D 307/64* (2006.01)

(52) U.S. Cl.
CPC ............. *A61K 31/34* (2013.01); *C07D 409/12* (2013.01); *A61K 31/36* (2013.01); *A61K 31/38* (2013.01); *C07D 333/34* (2013.01); *C07D 307/64* (2013.01)
USPC ...................................... 514/444

(58) Field of Classification Search
CPC .................................... A61K 31/34
USPC ......................................... 514/444
See application file for complete search history.

(56) References Cited

U.S. PATENT DOCUMENTS 7,541,381 B2   6/2009   Shoichet et al.

FOREIGN PATENT DOCUMENTS

| WO | 02/06246 | 1/2002 |
| WO | 2009/017719 | 2/2009 |
| WO | 2010-013071 | 2/2010 |

OTHER PUBLICATIONS

King, Med. Chem., (1994) pp. 206-208.*
Bedard, K., et al. "Small Molecule Agonists of the RIG-I Pathway and their Potent Antiviral Actions," Antiviral Research, Elsevier BV, NL, vol. 86, No. 1, p. A25, (Apr. 1, 2010).
Search Report for EP Application No. 11772681 dated Oct. 30, 2013.
Search Report for PCT/US11/033338 dated Jan. 18, 2012.
Tondi, D., et al., "Structure-Based Optimization of a Non-[beta]-lactam Lead Results in Inhibitors That Do Not Up-Regulate [beta]-Lactamase Expression in Cell Culture," Journal of the American Chemical Society, vol. 127, pp. 4632-4639 (Apr. 1, 2005).
Banerjee, S., et al. (2008) Multi-targeted therapy of cancer by genistein, Cancer Lett 269, 226-242.
Barnard, D. L. (2009) Animal models for the study of influenza pathogenesis and therapy, Antiviral Res 82, A110-122.
Blight, J.J. et al., (2002) Highly Permissive Cell Lines for Subgenomic and Genomic Hepatitis C Virus RNA Replication, J. Virology 76:13001-13014.
Daffis, S., et al. (2008) Toll-like receptor 3 has a protective role against West Nile virus infection, J Virol 82, 10349-10358.
Horsmans, Y., et al. (2005) Isatoribine, an agonist of TLR7, reduces plasma virus concentration in chronic hepatitis C infection, Hepatology 42, 724-731.
Johnson, C. L., and Gale, M., Jr. (2006) CARD games between virus and host get a new player, Trends Immunol 27, 1-4.
Kato, H., et al. (2006) Differential roles of MDA5 and RIG-I helicases in the recognition of RNA viruses, Nature 441, 101-105.
Kawai, T., et al. (2005) IPS-1, an adaptor triggering RIG-I- and Mda5-mediated type I interferon induction, Nat Immunol 6, 981-988.
Lee, J., et al. (2006) Activation of anti-hepatitis C virus responses via Toll-like receptor 7, Proc Natl Acad Sci U S A 103, 1828-1833.
Lescuyer, P., et al. (2003) Progress in the definition of a reference human mitochondrial proteome, Proteomics 3, 157-167.
Li, K., et al. (2005) Distinct poly(I-C) and virus-activated signaling pathways leading to interferon-beta production in hepatocytes, J Biol Chem 280, 16739-16747.
Lipinski, C. A., et al. (2001) Experimental and computational approaches to estimate solubility and permeability in drug discovery and development settings, Adv Drug Deliv Rev 46, 3-26.
Loo, Y. M., et al. (2008) Distinct RIG-I and MDA5 signaling by RNA viruses in innate immunity, J Virol 82, 335-345.
Loo, Y. M., et al. (2006) Viral and therapeutic control of IFN-beta promoter stimulator 1 during hepatitis C virus infection, Proc Natl Acad Sci U S A 103, 6001-6006.
Lutfalla, G., et al. (1995) Mutant U5A cells are complemented by an interferon-alpha beta receptor subunit generated by alternative processing of a new member of a cytokine receptor gene cluster, EMBO J 14, 5100-5108.
Meylan, E., et al. (2005) Cardif is an adaptor protein in the RIG-I antiviral pathway and is targeted by hepatitis C virus, Nature 437, 1167-1172.
Odaka, M., et al. (1997) Ligand-binding enhances the affinity of dimerization of the extracellular domain of the epidermal growth factor receptor, J Biochem 122, 116-121.
Paterniti, et al. (2010) Evidence for the Role of Peroxisome Proliferator-Activated Receptor-beta/delta in the Development of Spinal Cord Injury. Journa 1 of Pharmacology and Experimental Therapeutics, 333(2), pp. 465-477.

(Continued)

*Primary Examiner* — Taofiq A Solola
(74) *Attorney, Agent, or Firm* — Lee Hayes, PLLC; C. Rachal Winger

(57) ABSTRACT

Disclosed herein are compounds and related compositions for the treatment of viral infection, including RNA viral infection, and compounds that can modulate the RIG-I pathway in vertebrate cells, including compounds that can activate the RIG-I pathway.

7 Claims, 1 Drawing Sheet

(56) References Cited

OTHER PUBLICATIONS

Philo, J. S., et al. (1996) Dimerization of the extracellular domain of the erythropoietin (EPO) receptor by EPO: one high-affinity and one low-affinity interaction, Biochemistry 35, 1681-1691.

Philo, J. S., et al. (1996) Human stem cell factor dimer forms a complex with two molecules of the extracellular domain of its receptor, Kit, J Biol Chem 271, 6895-6902.

Renard, P., et al. (2001) Development of a sensitive multi-well colorimetric assay for active NFkappaB, Nucleic Acids Res 29, E21.

Saito, T., et al. (2007) Regulation of innate antiviral defenses through a shared repressor domain in RIG-I and LGP2, Proc Natl Acad Sci U S A 104, 582-587.

Saito, T., et al. (2008) Innate immunity induced by composition-dependent RIG-I recognition of hepatitis C virus RNA, Nature 454, 523-527.

Seth, R. B., et al. (2005) Identification and characterization of MAVS, a mitochondrial antiviral signaling protein that activates NF-kappaB and IRF 3, Cell 122, 669-682.

Sumpter, R., et al. (2005) Regulating intracellular antiviral defense and permissiveness to hepatitis C virus RNA replication through a cellular RNA helicase, RIG-I, J Virol 79, 2689-2699.

Suthar, M. S., et al. (2010) IPS-1 is essential for the control of West Nile virus infection and immunity, PLoS Pathog 6, e1000757.

Tan, S. L., et al. (2007) Systems biology and the host response to viral infection, Nat Biotechnol 25, 1383-1389.

Taylor, S. W., et al. (2003) Characterization of the human heart mitochondrial proteome, Nat Biotechnol 21, 281-286.

Venkataraman, T., et al. (2007) Loss of DExD/H box RNA helicase LGP2 manifests disparate antiviral responses, J Immunol 178, 6444-6455.

Xu, L. G., et al. (2005) VISA is an adapter protein required for virus-triggered IFN-beta signaling, Mol Cell 19, 727-740.

Yoneyama, M., et al. (2005) Shared and unique functions of the DExD/H-box helicases RIG-I, MDA5, and LGP2 in antiviral innate immunity, J Immunol 175, 2851-2858.

Yoneyama, M., et al. (2004) The RNA helicase RIG-I has an essential function in double-stranded RNA-induced innate antiviral responses, Nat Immunol 5, 730-737.

Zou, J., et al. (2009) Origin and evolution of the RIG-I like RNA helicase gene family, BMC Evol Biol 9, 85.

\* cited by examiner

SULFONAMIDE ANTI-VIRAL COMPOUNDS

STATEMENT OF GOVERNMENT INTEREST

This invention was made with government support under National Institutes of Health Grant No. AI081335. The government has certain rights in this invention.

FIELD OF THE DISCLOSURE

Compounds and methods disclosed herein are useful for treating viral infection in vertebrates, including RNA viral infections.

BACKGROUND OF THE DISCLOSURE

As a group, RNA viruses represent an enormous public health problem in the U.S. and worldwide. Well-known RNA viruses include influenza virus (including the avian and swine isolates), hepatitis C virus (HCV), West Nile virus, SARS-coronavirus, respiratory syncytial virus (RSV), and human immunodeficiency virus (HIV).

More than 170 million people worldwide are infected by HCV, and 130 million of those are chronic carriers at risk of developing chronic liver diseases (cirrhosis, carcinoma, and liver failure). As such, HCV is responsible for two thirds of all liver transplants in the developed world. Recent studies show that the death rate from HCV infection is rising due to the increasing age of chronically infected patients. Likewise seasonal flu infects 5-20% of the population resulting in 200,000 hospitalizations and 36,000 deaths each year.

Compared to influenza and HCV, West Nile virus causes the lowest number of infections, 981 in the United States in 2010. Twenty percent of infected patients develop a severe form of the disease, resulting in a 4.5% mortality rate. Unlike influenza and HCV, there are no approved therapies for the treatment of West Nile virus infection, and it is a high-priority pathogen for drug development due to its potential as a bioterrorist agent.

Among the RNA viruses listed, vaccines exist only for influenza virus. Accordingly, drug therapy is essential to mitigate the significant morbidity and mortality associated with these viruses. Unfortunately, the number of antiviral drugs is limited, many are poorly effective, and nearly all are plagued by the rapid evolution of viral resistance and a limited spectrum of action. Moreover, treatments for acute influenza and HCV infections are only moderately effective. The standard of care for HCV infection, PEGylated interferon and ribavirin, is effective in only 50% of patients, and there are a number of dose-limiting side effects associated with the combined therapy. Both classes of acute influenza antivirals, adamantanes and neuraminidase inhibitors, are only effective within the first 48 hours after infection, thereby limiting the window of opportunity for treatment. High resistance to adamantanes already restricts their use, and massive stockpiling of neuraminidase inhibitors will eventually lead to overuse and the emergence of resistant strains of influenza.

Most drug development efforts against these viruses target viral proteins. This is a large part of the reason that current drugs are narrow in spectrum and subject to the emergence of viral resistance. Most RNA viruses have small genomes and many encode less than a dozen proteins. Viral targets are therefore limited. Based on the foregoing, there is an immense and unmet need for effective treatments against viral infections.

SUMMARY OF THE DISCLOSURE

The compounds and methods disclosed herein shift the focus of viral drug development away from the targeting of viral proteins to the development of drugs that target and enhance the host's innate antiviral response. Such compounds and methods are likely to be more effective, less susceptible to the emergence of viral resistance, cause fewer side effects and be effective against a range of different viruses(1).

The RIG-I pathway is intimately involved in regulating the innate immune response to RNA virus infections. RIG-I agonists are expected to be useful for the treatment of many viruses including, without limitation, HCV, influenza, and West Nile virus. Accordingly, the present disclosure relates to compounds and methods for treating viral infection, including infection by RNA viruses, wherein the compounds can modulate the RIG-I pathway.

One embodiment includes a pharmaceutical composition comprising a compound having a structure

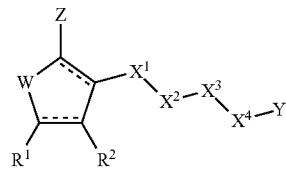

wherein W is S, O, NH, $NR^3$, $CR^3$=$CR^4$;

$R^1$ and $R^2$ are each independently selected from H, lower alkyl, aryl, alkenyl, alkynyl, alkylaryl, arylalkyl, alkoxy, aryloxy, arylalkoxy, alkoxyalkylaryl, alkylamino, aminoalkyl, dialkylamino, arylamino, aminoaryl, heteroalkyl, heteroaryl, heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazole, thiazole, isothiazole, imidazole, thiadiazole, thiadiazole S-oxide, thiadiazole S,S-dioxide, sulfonylamidine, sulfonylguanidine, sulfamoylamidine, sulfamoylguanidine, pyrazole, oxazole, isoxazole, pyridinyl, pyrimidinyl, piperazine, quinoline, isoquinoline, $SR^5$, $SOR^5$, $SO_2R^5$, $CO_2R^5$, $COR^5$, $CONR^5R^6$, $CSNR^5R^6$, $SO_mNR^5R^6$ or when two of $R^1$, $R^2$, $R^3$ and $R^4$ are taken together form cyclic groups including, but not limited to, methylene dioxo, benzo, morpholino, piperidinyl, dioxanyl, pyranyl, heteroaryl, furanyl, thiophene, pyrrole, thiazole, isothiazole, imidazole, oxazole, isoxazole, pyridinyl, pyrimidinyl or piperazine;

$X_1$ and $X_4$ are each independently $(CR^7R^8)_n$;

$X_2$ and $X_3$ are each independently $SO_2$, C=O, NH, $NR^9$;

m is 0, 1 or 2;

n is 0 to 8;

Y is substituted and unsubstituted aryl or substituted and unsubstituted heteroaryl of no more than three rings and if consisting of three rings no more than 2 are aromatic. The groups represented by Y include, but are not limited to, phenyl, pyridine, pyrimidine, pyrazine, pyridazine, pyrrole, pyrazole, imidazole, oxazole, isoxazole, thiazole, isothiazole, quinoline, isoquinoline, biphenyl or pyridyl phenyl;

Z is selected from H, lower alkyl, aryl, alkenyl, alkynyl, alkylaryl, arylalkyl, alkoxy, aryloxy, arylalkoxy, alkoxyalkylaryl, alkylamino, aminoalkyl, dialkylamino, arylamino, aminoaryl, heteroaryl, heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazole, thiazole, isothiazole, imidazole, thiadiazole, thiadiazole S-oxide, thiadiazole S,S-dioxide, sulfonylamidine, sulfonylguanidine, sulfamoylamidine, sulfamoylguanidine, pyrazole, oxazole, isoxazole, pyridinyl, pyrimidinyl, piperazine, quinoline, isoquinoline, $SR^5$, $SOR^5$, $SO_2R^5$, $CO_2R^5$, $COR^5$, $CONR^5R^6$, $CSNR^5R^6$, $SO_mNR^5R^6$; and $R^5$, $R^6$, $R^7$, $R^8$ and $R^9$ are each independently selected from H, lower alkyl, aryl, alkenyl, alkynyl, alkylaryl, arylalkyl, alkoxy, aryloxy, arylalkoxy, heteroalkyl, heteroaryl, heteroarylalkyl, cyclic heteroalkyl or cyclic heteroalkylalkyl.

Dashed lines indicate single or double bonds.

Another embodiment includes a pharmaceutical composition comprising a compound described above or a pharmaceutically acceptable salt, tautomer, isomer and/or prodrug thereof.

In another embodiment, the compound has a formula

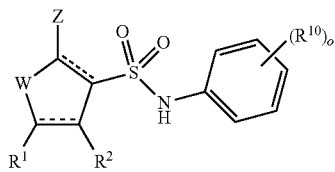

wherein $R^{10}$ is H, lower alkyl, aryl, alkenyl, alkynyl, alkylaryl, arylalkyl, alkoxy, aryloxy, arylalkoxy, alkoxyalkylaryl, alkylamino, aminoalkyl, dialkylamino, arylamino, aminoaryl, heteroalkyl, heteroaryl, heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazole, thiazole, isothiazole, imidazole, thiadiazole, thiadiazole S-oxide, thiadiazole S,S-dioxide, sulfonylamidine, sulfonylguanidine, sulfamoylamidine, sulfamoylguanidine, pyrazole, oxazole, isoxazole, pyridinyl, pyrimidinyl, piperazine, quinoline, isoquinoline, $SR^5$, $SOR^5$, $SO_2R^5$, $CO_2R^5$, $COR^5$, $CONR^5R^6$, $CSNR^5R^6$, $SO_mNR^5R^6$ or when two adjacent $R^{10}$ are taken together form cyclic groups including, but not limited to, methylene dioxo, benzo, morpholino, piperidinyl, dioxanyl, pyranyl, heteroaryl, furanyl, thiophene, pyrrole, thiazole, isothiazole, imidazole, oxazole, isoxazole, pyridinyl, pyrimidinyl or piperazine; and o is 1, 2, 3, 4 or 5.

In another embodiment, the compound has a formula

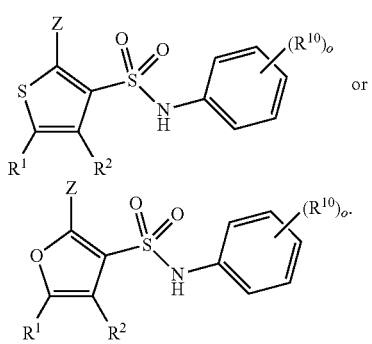

In another embodiment, the compound has a formula

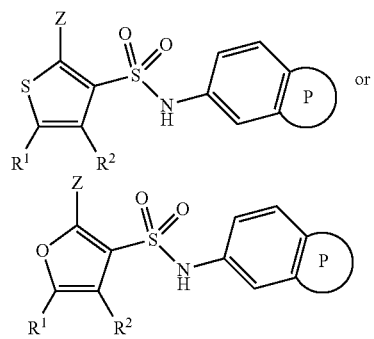

wherein ring P is a substituted or non-substituted methylene dioxo, benzo, morpholino, piperidinyl, dioxanyl, pyranyl, heteroaryl, furanyl, thiophene, pyrrole, thiazole, isothiazole, imidazole, oxazole, isoxazole, pyridinyl, pyrimidinyl or piperazine.

In another embodiment, the compound has a formula

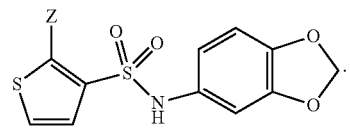

In another embodiment, the compound has a formula

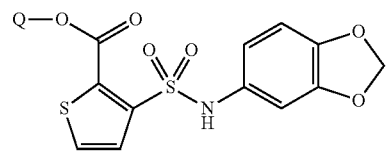

wherein Q is H or lower alkyl.

In another embodiment, the compound has a formula

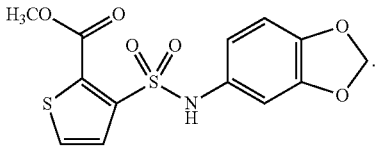

Another embodiment includes a method of treating or preventing a viral infection in a vertebrate comprising administering a pharmaceutical composition comprising a compound described above.

In another embodiment, the viral infection is caused by a virus from one or more of the following families: Arenaviridae, Astroviridae, Birnaviridae, Bromoviridae, Bunyaviridae, Caliciviridae, Closteroviridae, Comoviridae, Cystoviridae, Flaviviridae, Flexiviridae, Hepevirus, Leviviridae, Luteoviridae, Mononegavirales, Mosaic Viruses, Nidovirales, Nodaviridae, Orthomyxoviridae, Picobirnavirus, Picornaviridae, Potyviridae, Reoviridae, Retroviridae, Sequiviridae, Tenuivirus, Togaviridae, Tombusviridae, Totiviridae, Tymoviridae, Hepadnaviridae, Herpesviridae, Paramyxoviridae or Papillomaviridae.

In another embodiment, the viral infection is influenza virus, Hepatitis C virus, West Nile virus, SARS-coronavirus, poliovirus, measles virus, Dengue virus, yellow fever virus, tick-borne encephalitis virus, Japanese encephalitis virus, St. Louis encephalitis virus, Murray Valley virus, Powassan virus, Rocio virus, louping-ill virus, Banzi virus, Ilheus virus, Kokobera virus, Kunjin virus, Alfuy virus, bovine diarrhea virus, Kyasanur forest disease virus or human immunodeficiency virus (HIV).

In another embodiment of the methods disclosed herein, the compound has a formula

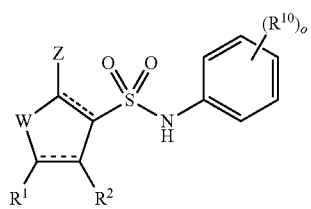

wherein $R^{10}$ is H, lower alkyl, aryl, alkenyl, alkynyl, alkylaryl, arylalkyl, alkoxy, aryloxy, arylalkoxy, alkoxyalkylaryl, alkylamino, aminoalkyl, dialkylamino, arylamino, aminoaryl, heteroalkyl, heteroaryl, heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazole, thiazole, isothiazole, imidazole, thiadiazole, thiadiazole S-oxide, thiadiazole S,S-dioxide, sulfonylamidine, sulfonylguanidine, sulfamoylamidine, sulfamoylguanidine, pyrazole, oxazole, isoxazole, pyridinyl, pyrimidinyl, piperazine, quinoline, isoquinoline, $SR^5$, $SOR^5$, $SO_2R^5$, $CO_2R^5$, $COR^5$, $CONR^5R^6$, $CSNR^5R^6$, $SO_mNR^5R^6$ or when two adjacent $R^{10}$ are taken together form cyclic groups including, but not limited to, methylene dioxo, benzo, morpholino, piperidinyl, dioxanyl, pyranyl, heteroaryl, furanyl, thiophene, pyrrole, thiazole, isothiazole, imidazole, oxazole, isoxazole, pyridinyl, pyrimidinyl or piperazine; and o is 1, 2, 3, 4 or 5.

In another embodiment of the methods disclosed herein, the compound has a formula

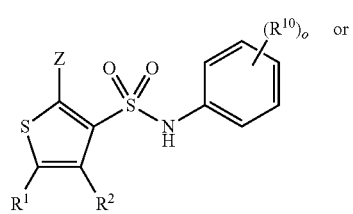

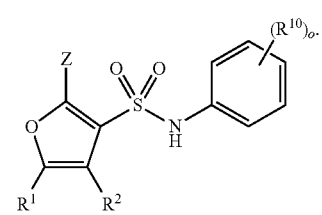

In another embodiment of the methods disclosed herein, the compound has a formula

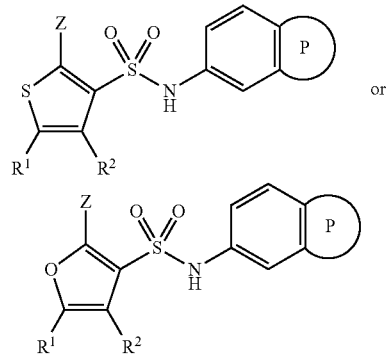

wherein ring P is a substituted or non-substituted methylene dioxo, benzo, morpholino, piperidinyl, dioxanyl, pyranyl, heteroaryl, furanyl, thiophene, pyrrole, thiazole, isothiazole, imidazole, oxazole, isoxazole, pyridinyl, pyrimidinyl or piperazine.

15. A pharmaceutical composition of claim 2 wherein the compound has a formula

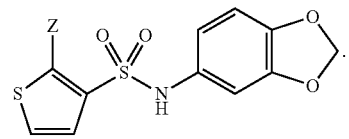

In another embodiment of the methods disclosed herein, the compound has a formula

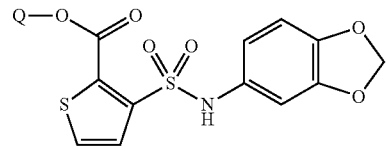

wherein Q is H or lower alkyl.

In another embodiment of the methods disclosed herein, the compound has a formula

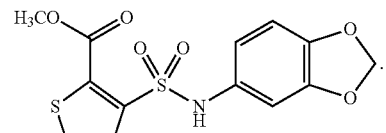

In another embodiment of the methods disclosed herein, the method further comprises vaccinating a vertebrate by additionally administering a vaccine against influenza virus, Hepatitis C virus, West Nile virus, SARS-coronavirus, poliovirus, measles virus, Dengue virus, yellow fever virus, tick-borne encephalitis virus, Japanese encephalitis virus, St. Louis encephalitis virus, Murray Valley virus, Powassan virus, Rocio virus, louping-ill virus, Banzi virus, Ilheus virus, Kokobera virus, Kunjin virus, Alfuy virus, bovine diarrhea virus, Kyasanur forest disease virus or human immunodeficiency virus (HIV).

Another embodiment includes a method of modulating the innate immune response in a eukaryotic cell, comprising administering to the cell a compound described above.

In another embodiment of modulating the innate immune response in a eukaryotic cell, the compound has a formula

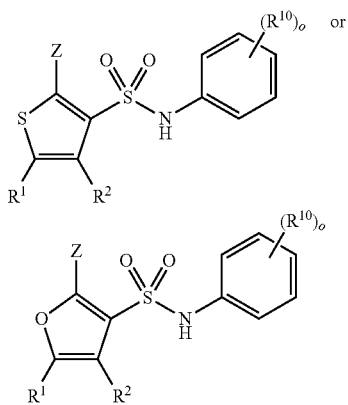

DETAILED DESCRIPTION

Figure 1A:
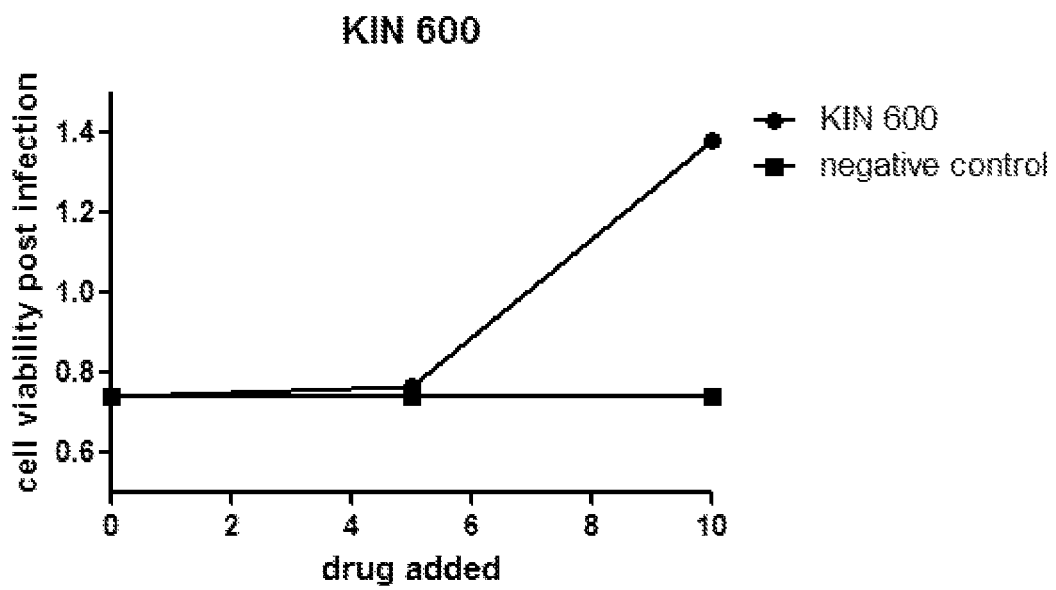
FIGS. 1A and 1B show the effect of KIN600 and positive control on cell viability following infection with Murine Encephalomyocarditis virus (EMCV).

The present disclosure provides compounds and methods that shift the focus of viral treatments away from the targeting of viral proteins to the development of drugs that target and enhance the host (patient's) innate antiviral response. Such compounds and methods are likely to be more effective, less susceptible to the emergence of viral resistance, cause fewer side effects and be effective against a range of different viruses (1).

The RIG-I pathway is intimately involved in regulating the innate immune response to RNA virus infections. RIG-I is a cytosolic pathogen recognition receptor that is essential for triggering immunity to a wide range of RNA viruses (5-8). RIG-I is a double-stranded RNA helicase that binds to motifs within the RNA virus genome characterized by homopolymeric stretches of uridine or polymeric U/A motifs (9). Binding to RNA induces a conformation change that relieves RIG-I signaling repression by an autologous repressor domain, thus allowing RIG-I to signal downstream through its tandem caspase activation and recruitment domains (CARDs) (4). RIG-I signaling is dependent upon its NTPase activity, but does not require the helicase domain (10μ, 11). RIG-I signaling is silent in resting cells, and the repressor domain serves as the on-off switch that governs signaling in response to virus infection (8).

RIG-I signaling is transduced through IPS-1 (also known as Cardif, MAVs, and VISA), an essential adaptor protein that resides in the outer mitochondrial membrane (12-15). IPS-1 recruits a macromolecular signaling complex that stimulates the downstream activation of IRF-3, a transcription factor that induces the expression of type I IFNs and virus-responsive genes that control infection (16). Compounds that trigger RIG-I signaling directly or through modulation of RIG-I pathway components, including IRF-3, present attractive therapeutic applications as antivirals or immune modulators.

A high-throughput screening approach was used to identify compounds that modulate the RIG-I pathway, a key regulator of the cellular innate immune response to RNA virus infection. In particular embodiments, validated RIG-I agonist lead compounds were demonstrated to specifically activate interferon regulatory factor-3 (IRF-3). In additional embodiments they exhibit one or more of the following: they induce the expression of interferon-stimulated genes (ISGs), have low cytotoxicity in cell-based assays, are suitable for analog development and QSAR studies, have drug-like physiochemical properties, and have antiviral activity against influenza A virus and/or hepatitis C virus (HCV). In certain embodiments, the compounds exhibit all of these characteristics.

As discussed below, these compounds represent a new class of potential antiviral therapeutics. Although the disclosure is not bound by a specific mechanism of action of the compounds in vivo, the compounds are selected for their modulation of the RIG-I pathway. In certain embodiments, the modulation is activation of the RIG-I pathway. Compounds and methods disclosed herein function to, one or more of, decrease viral protein, viral RNA, and infectious virus in cell culture models of HCV and/or influenza virus.

In one embodiment, the disclosure herein relates to a class of compounds of the following structures:

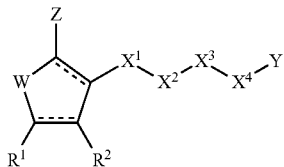

wherein W is S, O, NH, $NR^3$ or $CR^3=CR^4$;

$R^1$ and $R^2$ are each independently selected from H, lower alkyl, aryl, alkenyl, alkynyl, alkylaryl, arylalkyl, alkoxy, aryloxy, arylalkoxy, alkoxyalkylaryl, alkylamino, aminoalkyl, dialkylamino, arylamino, aminoaryl, heteroalkyl, heteroaryl, heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazole, thiazole, isothiazole, imidazole, thiadiazole, thiadiazole S-oxide, thiadiazole S,S-dioxide, sulfonylamidine, sulfonylguanidine, sulfamoylamidine, sulfamoylguanidine, pyrazole, oxazole, isoxazole, pyridinyl, pyrimidinyl, piperazine, quinoline, isoquinoline, $SR^5$, $SOR^5$, $SO_2R^5$, $CO_2R^5$, $COR^5$, $CONR^5R^6$, $CSNR^5R^6$, $SO_mNR^5R^6$ or when two of $R^1$, $R^2$, $R^3$ and $R^4$ are taken together form cyclic groups including, but not limited to, methylene dioxo, benzo, morpholino, piperidinyl, dioxanyl, pyranyl, heteroaryl, furanyl, thiophene, pyrrole, thiazole, isothiazole, imidazole, oxazole, isoxazole, pyridinyl, pyrimidinyl or piperazine;

$X_1$ and $X_4$ are each independently $(CR^7R^8)_n$;

$X_2$ and $X_3$ are each independently $SO_2$, C=O, NH or $NR^9$;

m is 0, 1 or 2;

n is 0 to 8;

Y is substituted and unsubstituted aryl or substituted and unsubstituted heteroaryl of no more than three rings and if consisting of three rings no more than 2 are aromatic. The groups represented by Y include, but are not limited to, phenyl, pyridine, pyrimidine, pyrazine, pyridazine, pyrrole, pyrazole, imidazole, oxazole, isoxazole, thiazole, isothiazole, quinoline, isoquinoline, biphenyl or pyridyl phenyl;

Z is selected from H, lower alkyl, aryl, alkenyl, alkynyl, alkylaryl, arylalkyl, alkoxy, aryloxy, arylalkoxy, alkoxyalkylaryl, alkylamino, aminoalkyl, dialkylamino, arylamino, aminoaryl, heteroalkyl, heteroaryl, heteroarylalkyl, cyclic heteroalkyl, cyclic heteroalkylalkyl, acyl, $NH_2$, $NR^5R^6$, OH, $OR^S$, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazole, thiazole, isothiazole, imidazole, thiadiazole, thiadiazole S-oxide, thiadiazole S,S-dioxide, sulfonylamidine, sulfonylguanidine, sulfamoylamidine, sulfamoylguanidine, pyrazole, oxazole, isoxazole, pyridinyl, pyrimidinyl, piperazine, quinoline, isoquinoline, $SR^5$, $SOR^5$, $SO_2R^5$, $CO_2R^5$, $COR^5$, $CONR^5R^6$, $CSNR^5R^6$, $SO_mNR^5R^6$; and $R^5$, $R^6$, $R^7$, $R^8$ and $R^9$ are each independently selected from H, lower alkyl, aryl, alkenyl, alkynyl, alkylaryl, arylalkyl, alkoxy, aryloxy, arylalkoxy, heteroalkyl, heteroaryl, heteroarylalkyl, cyclic heteroalkyl or cyclic heteroalkylalkyl.

Dashed lines can be single or double bonds

Pharmaceutically acceptable salts, tautomers, isomers and prodrugs of the compounds above are considered to be within the scope of the present description.

In another embodiment, the compounds have a structure

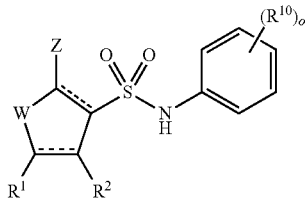

wherein $R^{10}$ is H, lower alkyl, aryl, alkenyl, alkynyl, alkylaryl, arylalkyl, alkoxy, aryloxy, arylalkoxy, alkoxyalkylaryl, alkylamino, aminoalkyl, dialkylamino, arylamino, aminoaryl, heteroalkyl, heteroaryl, heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazole, thiazole, isothiazole, imidazole, thiadiazole, thiadiazole S-oxide, thiadiazole S,S-dioxide, sulfonylamidine, sulfonylguanidine, sulfamoylamidine, sulfamoylguanidine, pyrazole, oxazole, isoxazole, pyridinyl, pyrimidinyl, piperazine, quinoline, isoquinoline, $SR^5$, $SOR^5$, $SO_2R^5$, $CO_2R^5$, $COR^5$, $CONR^5R^6$, $CSNR^5R^6$, $SO_mNR^5R^6$ or when two adjacent $R^{10}$ are taken together form cyclic groups including, but not limited to, methylene dioxo, benzo, morpholino, piperidinyl, dioxanyl, pyranyl, heteroaryl, furanyl, thiophene, pyrrole, thiazole, isothiazole, imidazole, oxazole, isoxazole, pyridinyl, pyrimidinyl or piperazine; and o is 1, 2, 3, 4 or 5.

In yet further embodiments, the compounds have a structure

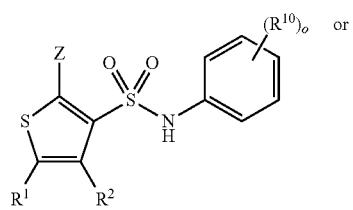

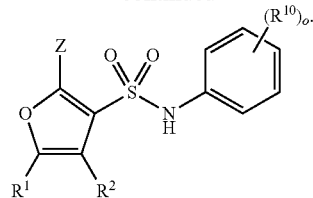

In one embodiment, the compounds have a structure

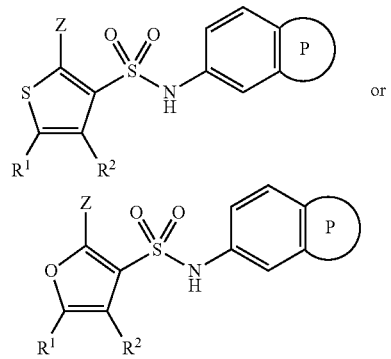

wherein ring P is a substituted or non-substituted methylene dioxo, benzo, morpholino, piperidinyl, dioxanyl, pyranyl, heteroaryl, furanyl, thiophene, pyrrole, thiazole, isothiazole, imidazole, oxazole, isoxazole, pyridinyl, pyrimidinyl or piperazine.

Even further still, in some embodiments, the compounds have a structure

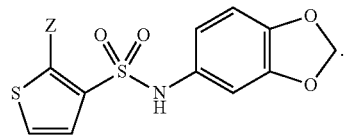

In one example embodiment, the compounds have a structure

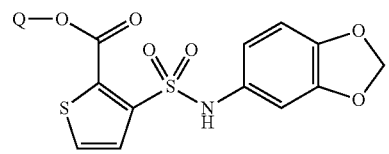

wherein Q is H or lower alkyl.

In one embodiment, the compounds have a structure (KIN600):

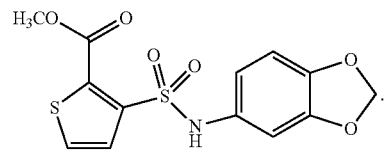 [SMILES: COC(=O)c1sccc1S(=O)(=O)Nc1ccc2c(c1)OCO2]

In other embodiments, the compounds have a structure selected from
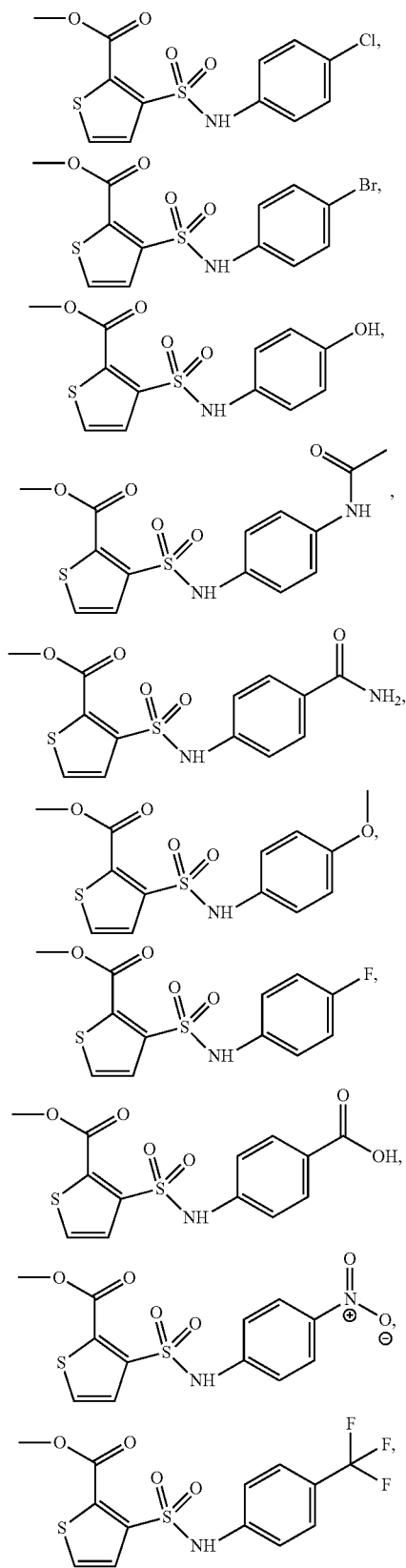
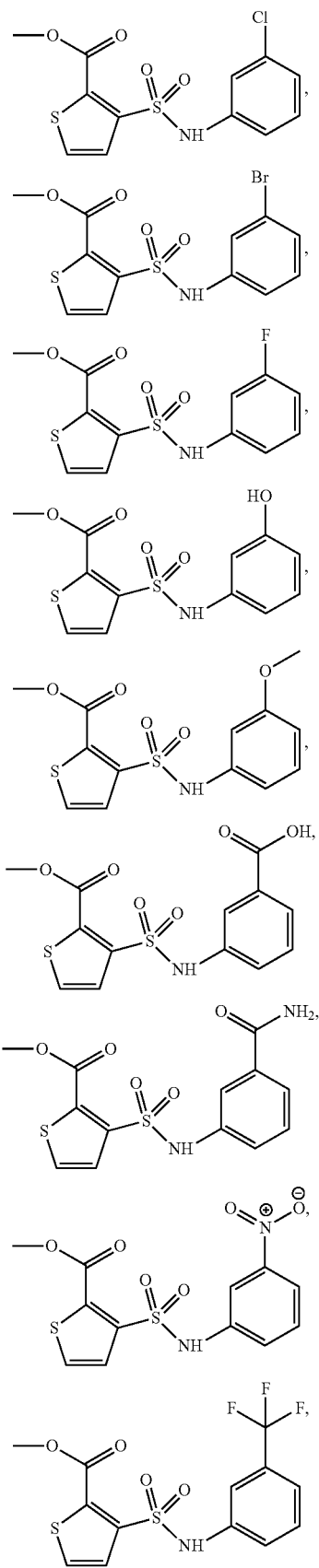

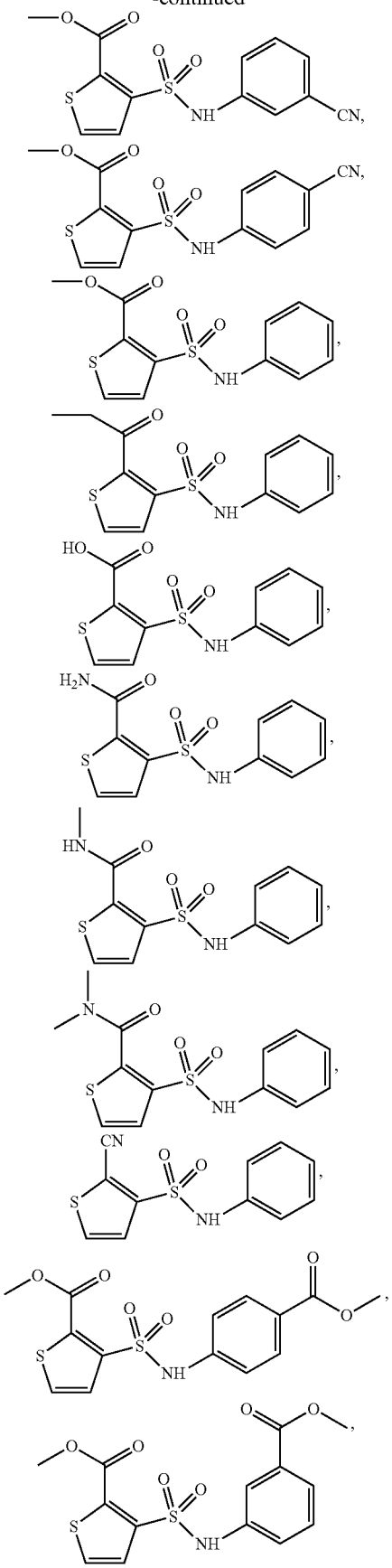

As used herein, either alone or in combination, the terms "alkyloxy" or "alkoxy" refer to a functional group comprising an alkyl ether group. Examples of alkoxys include, without limitation, methoxy, ethoxy, n-propoxy, isopropoxy, n-butoxy, iso-butoxy, sec-butoxy, tert-butoxy, and the like.

The terms "alkyl", "alkenyl", and "alkynyl" refer to substituted and unsubstituted alkyls, alkenyls and alkynyls. The term "alkyl" refers to a functional group comprising a straight-chain or branched-chain hydrocarbon containing from 1 to 20 carbon atoms linked exclusively by single bonds and not having any cyclic structure. An alkyl group may be optionally substituted as defined herein. Examples of alkyl groups includes, without limitation methyl, ethyl, n-propyl, isopropyl, n-butyl, isobutyl, sec-butyl, tert-butyl, pentyl, isoamyl, hexyl, heptyl, octyl, noyl, decyl, undecyl, dodecyl tridecyl, tetradecyl, pentadecyl, hexadecyl, heptadecyl, octadecyl, nonadecyl, eicosyl, and the like.

Substituted alkyls, alkenyls and alkynyls refers to alkyls, alkenyls and alkynyls substituted with one to five substituents from the group including H, lower alkyl, aryl, alkenyl, alkynyl, arylalkyl, alkoxy, aryloxy, arylalkoxy, alkoxyalkylaryl, alkylamino, arylamino, $NH_2$, OH, CN, $NO_2$, $OCF_3$, $CF_3$, F, 1-amidine, 2-amidine, alkylcarbonyl, morpholinyl, piperidinyl, dioxanyl, pyranyl, heteroaryl, furanyl, thiophenyl, tetrazolo, thiazolyl, isothiazolyl, imidazolyl, thiadiazolyl, thiadiazole S-oxide, thiadiazole S,S-dioxide, pyrazolo, oxazolyl, isoxazolyl, pyridinyl, pyrimidinyl, quinolinyl, isoquinolinyl, SR, SOR, $SO_2R$, $CO2R$, COR, CONR'R", CSNR'R", SOnNR'R".

As used herein, either alone or in combination, the term "alkynyl" refers to a functional group comprising a straight-chain or branched-chain hydrocarbon containing from 2 to 20 carbon atoms and having one or more carbon-carbon triple bonds and not having any cyclic structure. An alkynyl group may be optionally substituted as defined herein. Examples of alkynyl groups include, without limitation, ethynyl, propynyl, hydroxypropynyl, butynyl, butyn-1-yl, butyn-2-yl, 3-methylbutyn-1-yl, pentynyl, pentyn-1-yl, hexynyl, hexyn-2-yl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, and the like.

The term "alkylene," as used herein, alone or in combination, refers to a saturated aliphatic group derived from a straight or branched chain saturated hydrocarbon attached at two or more positions, such as methylene (—C2-). Unless otherwise specified, the term "alkyl" may include "alkylene" groups.

As used herein, either alone or in combination, the term "alkylcarbonyl" or "alkanoyl" refers to a functional group comprising an alkyl group attached to the parent molecular moiety through a carbonyl group. Examples of alkylcarbonyl groups include, without limitation, methylcarbonyl, ethylcarbonyl, and the like.

The term "alkynylene" refers to a carbon-carbon triple bond attached at two positions such as ethynylene (—C:::C—, —C≡C—). Unless otherwise specified, the term "alkynyl" may include "alkynylene" groups.

As used herein, either alone or in combination, the term "aryl", "hydrocarbyl aryl", or "aryl hydrocarbon" refers to a functional group comprising a substituted or unsubstituted aromatic hydrocarbon with a conjugated cyclic molecular ring structure of 3 to 12 carbon atoms. An aryl group can be monocyclic, bicyclic or polycyclic, and may optionally include one to three additional ring structures, such as, e.g., a cycloalkyl, a cycloalkenyl, a heterocycloalkyl, a heterocycloalkenyl, or a heteroaryl. The term "aryl" includes, without limitation, phenyl (benzenyl), thiophenyl, indolyl, naphthyl, totyl, xylyl, anthracenyl, phenanthryl, azulenyl, biphenyl, naphthalenyl, 1-mMethylnaphthalenyl, acenaphthenyl, acenaphthylenyl, anthracenyl, fluorenyl, phenalenyl, phenanthrenyl, benzo[a]anthracenyl, benzo[c]phenanthrenyl, chrysenyl, fluoranthenyl, pyrenyl, tetracenyl (naphthacenyl), triphenylenyl, anthanthrenyl, benzopyrenyl, benzo[a]pyrenyl, benzo[e]fluoranthenyl, benzo[ghi]perylenyl, benzo[j]fluoranthenyl, benzo[k]fluoranthenyl, corannulenyl, coronenyl, dicoronylenyl, helicenyl, heptacenyl, hexacenyl, ovalenyl, pentacenyl, picenyl, perylenyl, and tetraphenylenyl. Substituted aryl refers to aryls substituted with one to five substituents from the group including H, lower alkyl, aryl, alkenyl, alkynyl, arylalkyl, alkoxy, aryloxy, arylalkoxy, alkoxyalkylaryl, alkylamino, arylamino, NH$_2$, OH, CN, NO$_2$, OCF$_3$, CF$_3$, Br, Cl, F, 1-amidino, 2-amidino, alkylcarbonyl, morpholino, piperidinyl, dioxanyl, pyranyl, heteroaryl, furanyl, thiophenyl, tetrazolo, thiazole, isothiazolo, imidazolo, thiadiazole, thiadiazole S-oxide, thiadiazole S,S-dioxide, pyrazolo, oxazole, isoxazole, pyridinyl, pyrimidinyl, quinoline, isoquinoline, SR, SOR, SO$_2$R, CO$_2$R, COR, CONRR, CSNRR, SOnNRR.

As used herein, either alone or in combination, the term "lower aryl" refers to a functional group comprising a substituted or unsubstituted aromatic hydrocarbon with a conjugated cyclic molecular ring structure of 3 to 6 carbon atoms. Examples of lower aryl groups include, without limitation, phenyl and naphthyl.

As used herein, either alone or in combination, the term "carboxyl" or "carboxy" refers to the functional group —C(=O)OH or the corresponding "carboxylate" anion —C(=O)O—. Examples include, without limitation, formic acid, acetic acid, oxalic acid, benzoic acid. An "O-carboxyl" group refers to a carboxyl group having the general formula RCOO, wherein R is an organic moiety or group. A "C-carboxyl" group refers to a carboxyl group having the general formula COOR, wherein R is an organic moiety or group.

As used herein, either alone or in combination, the term "cycloalkyl", "carbocyclicalkyl", and "carbocyclealkyl" refers to a functional group comprising a substituted or unsubstituted non-aromatic hydrocarbon with a non-conjugated cyclic molecular ring structure of 3 to 12 carbon atoms linked exclusively with carbon-carbon single bonds in the carbon ring structure. A cycloalkyl group can be monocyclic, bicyclic or polycyclic, and may optionally include one to three additional ring structures, such as, e.g., an aryl, a heteroaryl, a cycloalkenyl, a heterocycloalkyl, or a heterocycloalkenyl.

As used herein, either alone or in combination, the term "lower cycloalkyl" refers to a functional group comprising a monocyclic substituted or unsubstituted non-aromatic hydrocarbon with a non-conjugated cyclic molecular ring structure of 3 to 6 carbon atoms linked exclusively with carbon-carbon single bonds in the carbon ring structure. Examples of lower cycloalkyl groups include, without limitation, cyclopropyl, cyclobutyl, cyclopentyl, and cyclohexyl.

As used herein, the term "functional group" refers to a specific group of atoms within a molecule that are responsible for the characteristic chemical reactions of those molecules.

As used herein, either alone or in combination, the term "heteroalkyl" refers to a functional group comprising a straight-chain or branched-chain hydrocarbon containing from 1 to 20 atoms linked exclusively by single bonds, where at least one atom in the chain is a carbon and at least one atom in the chain is O, S, N, or any combination thereof. The heteroalkyl group can be fully saturated or contain from 1 to 3 degrees of unsaturation. The non-carbon atoms can be at any interior position of the heteroalkyl group, and up to two non-carbon atoms may be consecutive, such as, e.g., —CH2—NH—OCH3. In addition, the non-carbon atoms may optionally be oxidized and the nitrogen may optionally be quaternized.

As used herein, either alone or in combination, the term "heteroaryl" refers to a functional group comprising a substituted or unsubstituted aromatic hydrocarbon with a conjugated cyclic molecular ring structure of 3 to 12 atoms, where at least one atom in the ring structure is a carbon and at least one atom in the ring structure is O, S, N, or any combination thereof. A heteroaryl group can be monocyclic, bicyclic or polycyclic, and may optionally include one to three additional ring structures, such as, e.g., an aryl, a cycloalkyl, a cycloalkenyl, a heterocycloalkyl, or a heterocycloalkenyl. Examples of heteroaryl groups include, without limitation, acridinyl, benzidolyl, benzimidazolyl, benzisoxazolyl, benzodioxinyl, dihydrobenzodioxinyl, benzodioxolyl, 1,3-benzodioxolyl, benzofuryl, benzoisoxazolyl, benzopyranyl, benzothiophenyl, benzo[c]thiophenyl, benzotriazolyl, benzoxadiazolyl, benzoxazolyl, benzothiadiazolyl, benzothiazolyl, benzothienyl, carbazolyl, chromonyl, cinnolinyl, dihydrocinnolinyl, coumarinyl, dibenzofuranyl, furopyridinyl, furyl, indolizinyl, indolyl, dihydroindolyl, imidazolyl, indazolyl, isobenzofuryl, isoindolyl, isoindolinyl, dihydroisoindolyl, isoquinolyl, dihydroisoquinolinyl, isoxazolyl, isothiazolyl, oxazolyl, oxadiazolyl, phenanthrolinyl, phenanthridinyl, purinyl, pyranyl, pyrazinyl, pyrazolyl, pyridyl, pyrimidinyl, pyridazinyl, pyrrolinyl, pyrrolyl, pyrrolopyridinyl, quinolyl, quinoxalinyl, quinazolinyl, tetrahydroquinolinyl, tetrazolopyridazinyl, tetrahydroisoquinolinyl, thiophenyl, thiazolyl, thiadiazolyl, thienopyridinyl, thienyl, thiophenyl, triazolyl, xanthenyl, and the like.

As used herein, either alone or in combination, the term "lower heteroaryl" refers to a functional group comprising a monocyclic or bicyclic, substituted or unsubstituted aromatic hydrocarbon with a conjugated cyclic molecular ring structure of 3 to 6 atoms, where at least one atom in the ring structure is a carbon and at least one atom in the ring structure is O, S, N, or any combination thereof.

As used herein, either alone or in combination, the term "hydroxy" refers to the functional group hydroxyl (—OH).

As used herein, either alone or in combination, the term "oxo" refers to the functional group =O.

As used herein, the term "vertebrate" includes all living vertebrates such as, without limitation, mammals, humans, birds, dogs, cats, livestock, farm animals, free-range herds, etc.

As used herein, a "pharmaceutical composition" comprises at least one compound disclosed herein together with one or more pharmaceutically acceptable carriers, excipients or diluents, as appropriate for the chosen mode of administration.

The pharmaceutical compositions can be made up in, without limitation, a solid form (including granules, powders or suppositories) or in a liquid form (e.g., solutions, suspensions, or emulsions). The pharmaceutical compositions can be subjected to conventional pharmaceutical operations such as sterilization and/or can contain conventional adjuvants, such as preservatives, stabilizers, wetting agents, emulsifiers, buffers etc.

Solid dosage forms for oral administration can include capsules, tablets, pills, powders, and granules. In such solid dosage forms, the active compound can be admixed with at least one inert diluent such as sucrose, lactose, or starch. Such dosage forms can also comprise, as in normal practice, additional substances other than inert diluents, e.g., lubricating agents such as magnesium stearate. In the case of capsules, tablets, and pills, the dosage forms can also comprise buffering agents. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting, sweetening, flavoring, and perfuming agents. The pharmaceutical composition can contain more than one embodiment of the present invention. Preparations for oral administration can be suitably formulated to give controlled release of the active compound.

For buccal administration the compositions can take the form of tablets or lozenges formulated in conventional manner.

The compounds can be formulated for parenteral administration by injection e.g. by bolus injection or infusion. Formulations for injection can be presented in unit dosage form, e.g. in glass ampoule or multi dose containers, e.g. glass vials. The compositions for injection can take such forms as suspensions, solutions or emulsions in oily or aqueous vehicles, and can contain formulatory agents such as suspending, stabilising, preserving and/or dispersing agents. Alternatively, the active ingredient can be in powder form for constitution with a suitable vehicle, e.g. sterile pyrogen-free water, before use.

In addition to the formulations described above, the compounds can also be formulated as a depot preparation. Such long acting formulations can be administered by implantation or by intramuscular injection.

For nasal or pulmonary administration or any other administration by inhalation, the compounds for use according to the present invention are conveniently delivered in the form of an aerosol spray presentation for pressurized packs or a nebulizer, with the use of suitable propellant, e.g. dichlorodifluoromethane, trichlorofluoromethane, dichlorotetrafluoroethane, carbon dioxide or other suitable gas or mixture of gases.

Many RNA viruses share biochemical, regulatory, and signaling pathways. These viruses include but are not limited to influenza virus (including avian and swine isolates), Hepatitis C virus, West Nile virus, SARS-coronavirus, poliovirus, measles virus, Dengue virus, yellow fever virus, tick-borne encephalitis virus, Japanese encephalitis virus, St. Louis encephalitis virus, Murray Valley virus, Powassan virus, Rocio virus, louping-ill virus, Banzi virus, Ilheus virus, Kokobera virus, Kunjin virus, Alfuy virus, bovine diarrhea virus, and the Kyasanur forest disease virus. The compounds and methods disclosed herein can be used to treat these viruses.

Relevant taxonomic families of RNA viruses include, without limitation, Astroviridae, Birnaviridae, Bromoviridae, Caliciviridae, Closteroviridae, Comoviridae, Cystoviridae, Flaviviridae, Flexiviridae, Hepevirus, Leviviridae, Luteoviridae, Mononegavirales, Mosaic Viruses, Nidovirales, Nodaviridae, Orthomyxoviridae, Picobirnavirus, Picornaviridae, Potyviridae, Reoviridae, Retroviridae, Sequiviridae, Tenuivirus, Togaviridae, Tombusviridae, Totiviridae, and Tymoviridae. The compounds and methods disclosed herein can be used to treat viruses within these families of viruses as part of a pharmaceutically acceptable drug formulation. Other relevant virus families include, without limitation, Hepadnaviridae, Herpesviridae, Paramyxoviridae and Papillomaviridae.

The disclosure provides for a vaccine comprised of the compounds, alone or in combination with an antigen, for the purpose of preventing or treating disease in an animal including a vertebrate animal.

The disclosure provides for the use of the compounds as adjuvants.

The compounds and methods disclosed herein can be additive or synergistic with other therapies currently in development or use. For example, ribavirin and interferon-α provide an effective treatment for HCV infection when used in combination. Their efficacy in combination can exceed the efficacy of either drug product when used alone. The compositions of the disclosure can be administered alone or in combination or conjunction with interferon, ribavirin and/or a variety of small molecules that are being developed against both viral targets (viral proteases, viral polymerase, assembly of viral replication complexes) and host targets (host proteases required for viral processing, host kinases required for phosphorylation of viral targets such as NS5A, and inhibitors of host factors required to efficiently utilize the viral internal ribosome entry site, or IRES).

The compounds and methods disclosed herein could be used in combination or conjunction with, without limitation, adamantane inhibitors, neuraminidase inhibitors, alpha interferons, non-nucleoside or nucleoside polymerase inhibitors, NS5A inhibitors, antihistamines, protease inhibitors, helicase inhibitors, P7 inhibitors, entry inhibitors, IRES inhibitors, immune stimulators, HCV replication inhibitors, cyclophilin A inhibitors, A3 adenosine agonists, and microRNA suppressors.

Cytokines that could be administered in combination or conjunction with the compounds and methods disclosed herein include, without limitation, IL-2, IL-12, IL-23, IL-27, or IFN-γ. New HCV drugs that are or will be available for potential administration in combination or conjunction with the compounds and methods disclosed herein include, without limitation, ACH-1625 (Achillion); Glycosylated interferon (Alios Biopharma); ANA598, ANA773 (Anadys Pharm); ATI-0810 (Arisyn Therapeutics); AVL-181 (Avila Therapeutics); LOCTERON® (Biolex); CTS-1027 (Conatus); SD-101 (Dynavax Technologies); Clemizole (Eiger Biopharmaceuticals); GS-9190 (Gilead Sciences); GI-5005 (GlobalImmune BioPharma); Resiquimod/R-848 (Graceway Pharmaceuticals); Albinterferon alpha-2b (Human Genome Sciences); IDX-184, IDX-320, IDX-375 (Idenix); IMO-2125 (Idera Pharmaceuticals); INX-189 (Inhibitex); ITCA-638 (Intarcia Therapeutics); ITMN-191/RG7227 (Intermune);

ITX-5061, ITX-4520 (iTherx Pharmaceuticals); MB11362 (Metabasis Therapeutics); Bavituximab (Peregrine Pharmaceuticals); PSI-7977, RG7128, PSI-938 (Pharmasset); PHX1766 (Phenomix); Nitazoxanide/ALINIA® (Romark Laboratories); SP-30 (Samaritan Pharmaceuticals); SCV-07 (SciClone); SCY-635 (Scynexis); TT-033 (Tacere Therapeutics); Viramidine/taribavirin (Valeant Pharmaceuticals); Telaprevir, VCH-759, VCH-916, VCH-222, VX-500, VX-813 (Vertex Pharmaceuticals); and PEG-INF Lambda (Zymogenetics).

New influenza and West Nile virus drugs that are or will be available for potential administration in combination or conjunction with the compounds and methods disclosed herein include, without limitation, neuraminidase inhibitors (Peramivir, Laninamivir); triple therapy—neuraminidase inhibitors ribavirin, amantadine (ADS-8902); polymerase inhibitors (Favipiravir); reverse transcriptase inhibitor (ANX-201); inhaled chitosan (ANX-211); entry/binding inhibitors (Binding Site Mimetic, Flucide); entry inhibitor, (Fludase); fusion inhibitor, (MGAWN1 for West Nile); host cell inhibitors (lantibiotics); cleavage of RNA genome (RNAi, RNAse L); immune stimulators (Interferon, Alferon-LDO; Neurokinin) agonist, Homspera, Interferon Alferon N for West Nile); and TG21.

Other drugs for treatment of influenza and/or hepatitis that are available for potential administration in combination or conjunction with the compounds and methods disclosed herein include, without limitation:

TABLE 1

Hepatitis and influenza drugs

| Branded Name | Generic Name | Approved Indications |
| --- | --- | --- |
| Pegasys | PEGinterferon alfa-2a | Hepatitis C, Hepatitis B |
| Peg-Intron | PEGinterferon alfa-2b | Hepatitis C |
| Copegus | Ribavirin | Hepatitis C |
| Rebetol | Ribavirin | Hepatitis C |
| — | Ribavirin | Hepatitis C |
| Tamiflu | Oseltamivir | Influenza A, B, C |
| Relenza | Zanamivir | Influenza A, B, C |
| — | Amantadine | Influenza A |
| — | Rimantadine | Influenza A |

These agents can be incorporated as part of the same pharmaceutical composition or can be administered separately from the compounds of the disclosure, either concurrently or in accordance with another treatment schedule. In addition, the compounds or compositions of the disclosure.

The compounds and methods disclosed herein can be additive or synergistic with other compounds and methods to enable vaccine development. By virtue of their antiviral and immune enhancing properties, the compounds can be used to affect a prophylactic or therapeutic vaccination. The compounds need not be administered simultaneously or in combination with other vaccine components to be effective. The vaccine applications of the compounds are not limited to the prevention or treatment of virus infection but can encompass all therapeutic and prophylactic vaccine applications due to the general nature of the immune response elicited by the compounds.

As is understood by one of ordinary skill in the art, vaccines can be against viruses, bacterial infections, cancers, etc. and can include one or more of, without limitation, a live attenuated vaccine (LAIV), an inactivated vaccine (IIV; killed virus vaccine), a subunit (split vaccine); a sub-virion vaccine; a purified protein vaccine; or a DNA vaccine. Appropriate adjuvants include one or more of, without limitation, water/oil emulsions, non-ionic copolymer adjuvants, e.g., CRL 1005 (Optivax; Vaxcel Inc., Norcross, Ga.), aluminum phosphate, aluminum hydroxide, aqueous suspensions of aluminum and magnesium hydroxides, bacterial endotoxins, polynucleotides, polyelectrolytes, lipophilic adjuvants and synthetic muramyl dipeptide (norMDP) analogs such as N-acetyl-normuranyl-L-alanyl-D-isoglutamine, N-acetyl-muranyl-(6-O-stearoyl)-L-alanyl-D-isoglutamine or N-Glycol-muranyl-LalphaAbu-D-isoglutamine (Ciba-Geigy Ltd.).

The pharmaceutical composition comprising a compound of the disclosure can be formulated in a variety of forms, e.g., as a liquid, gel, lyophilized, or as a compressed solid. The preferred form will depend upon the particular indication being treated and will be apparent to one of ordinary skill in the art. In one embodiment, the disclosed RIG-I agonists include formulations for oral delivery that can be small-molecule drugs that employ straightforward medicinal chemistry processes.

The administration of the formulations of the present disclosure can be performed in a variety of ways, including, but not limited to, orally, subcutaneously, intravenously, intracerebrally, intranasally, transdermally, intraperitoneally, intramuscularly, intrapulmonary, intrathecally, vaginally, rectally, intraocularly, or in any other acceptable manner. The formulations can be administered continuously by infusion, although bolus injection is acceptable, using techniques well known in the art, such as pumps (e.g., subcutaneous osmotic pumps) or implantation. In some instances the formulations can be directly applied as a solution or spray.

An example of a pharmaceutical composition is a solution designed for parenteral administration. Although in many cases pharmaceutical solution formulations are provided in liquid form, appropriate for immediate use, such parenteral formulations can also be provided in frozen or in lyophilized form. In the former case, the composition must be thawed prior to use. The latter form is often used to enhance the stability of the active compound contained in the composition under a wider variety of storage conditions, as it is recognized by those or ordinary skill in the art that lyophilized preparations are generally more stable than their liquid counterparts. Such lyophilized preparations are reconstituted prior to use by the addition of one or more suitable pharmaceutically acceptable diluents such as, without limitation, sterile water for injection or sterile physiological saline solution.

Parenterals can be prepared for storage as lyophilized formulations or aqueous solutions by mixing, as appropriate, the compound having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic detergents, antioxidants and/or other miscellaneous additives.

Buffering agents help to maintain the pH in the range which approximates physiological conditions. They are typically present at a concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, histidine buffers and trimethylamine salts such as Tris.

Preservatives can be added to retard microbial growth, and are typically added in amounts of about 0.2%-1% (w/v). Suitable preservatives for use with the present disclosure include, without limitation, phenol, benzyl alcohol, meta-cresol, methyl paraben, propyl paraben, octadecyldimethylbenzyl ammonium chloride, benzalkonium halides (e.g., benzalkonium chloride, bromide or iodide), hexamethonium chloride, alkyl parabens such as methyl or propyl paraben, catechol, resorcinol, cyclohexanol and 3-pentanol.

Isotonicifiers can be added to ensure isotonicity of liquid compositions and include, without limitation, polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, alpha-monothioglycerol and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on the active compound weight.

Additional miscellaneous excipients include bulking agents or fillers (e.g., starch), chelating agents (e.g., EDTA), antioxidants (e.g., ascorbic acid, methionine, vitamin E) and cosolvents.

The active ingredient can also be entrapped in microcapsules prepared, for example, by coascervation techniques or by interfacial polymerization, for example hydroxymethylcellulose, gelatin or poly-(methylmethacylate) microcapsules, in colloidal drug delivery systems (for example liposomes, albumin microspheres, microemulsions, nanoparticles and nanocapsules) or in macroemulsions. Such techniques are disclosed in Remington, The Science and Practice of Pharmacy, 21$^{st}$ Ed., published by Lippincott Williams & Wilkins, A Wolters Kluwer Company, 2005.

Parenteral formulations to be used for in vivo administration generally are sterile. This is readily accomplished, for example, by filtration through sterile filtration membranes.

Suitable examples of sustained-release preparations include semi-permeable matrices of solid hydrophobic polymers containing the compound or composition, the matrices having a suitable form such as a film or microcapsules. Examples of sustained-release matrices include polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as the PROLEASE® technology or LUPRON DEPOT® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for long periods such as up to or over 100 days, certain hydrogels release compounds for shorter time periods.

Oral administration of the compounds and compositions is one intended practice of the disclosure. For oral administration, the pharmaceutical composition can be in solid or liquid form, e.g., in the form of a capsule, tablet, powder, granule, suspension, emulsion or solution. The pharmaceutical composition is preferably made in the form of a dosage unit containing a given amount of the active ingredient. A suitable daily dose for a human or other vertebrate can vary widely depending on the condition of the patient and other factors, but can be determined by persons of ordinary skill in the art using routine methods.

In solid dosage forms, the active compound can be admixed with at least one inert diluent such as sucrose, lactose, or starch. Such dosage forms can also comprise, as is normal practice, additional substances, e.g., lubricating agents such as magnesium stearate. In the case of capsules, tablets and pills, the dosage forms can also comprise buffering agents. Tablets and pills can additionally be prepared with enteric coatings.

The compounds or compositions can be admixed with adjuvants such as lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, they can be dissolved in saline, water, polyethylene glycol, propylene glycol, ethanol, oils (such as corn oil, peanut oil, cottonseed oil or sesame oil), tragacanth gum, and/or various buffers. Other adjuvants and modes of administration are well known in the pharmaceutical art. The carrier or diluent can include time delay material, such as glyceryl monostearate or glyceryl distearate alone or with a wax, or other materials well known in the art.

The Examples below describe the properties of the disclosed compounds. The Examples are included to demonstrate particular embodiments of the disclosure. It should be appreciated by those of ordinary skill in the art that the techniques disclosed in the Examples represent techniques and compositions discovered by the inventors to function well in the practice of the disclosure, and thus can be considered to constitute preferred modes for its practice. However, those of ordinary skill in the art should, in light of the present disclosure, appreciate that many changes can be made in the specific embodiments which are disclosed and still obtain a like or similar result without departing from the spirit and scope of the disclosure. For example, the Examples below provide in vitro methods for testing the compounds of the disclosure. Other in vitro virus infection models include but are not limited to flaviviruses such as bovine diarrheal virus, West Nile Virus, and GBV-C virus, other RNA viruses such as respiratory syncytial virus, and the HCV replicon systems (32). Furthermore, any appropriate cultured cell competent for viral replication can be utilized in the antiviral assays.

EXAMPLES

Example 1

Characterization and Antiviral Activity of KIN600

KIN600 compounds are assayed for antiviral properties against RNA viruses in cell culture, including Hepatitis C virus and Influenza A virus. KIN600 showed antiviral activity in the HCV IF antiviral assays, and no significant cytotoxicity. These and other assays are performed as described below.

MTS assay to determine cytotoxicity. Cultured human Huh7 cells are treated with increasing amounts of KIN600 or equivalent amounts of DMSO diluted in media for 24 hours to see their effect on cell viability. The proportion of viable cells is calculated using a cell viability assay that measures conversion of a tetrazolium compound [3-(4,5-dimethyl-2-yl)-5-(3-carboxymethoxyphenyl)-2-(4-sulfophenyl)-2H-tetrazolium, inner salt; MTS] to a colored formazan compound in live cells.

The conversion of MTS to formazan is detected in a 96-well microtiter plate reader, and the resulting optical densities can be plotted directly to estimate cell viability. Cell Titer One (Promega) is the one step reagent used according to manufacturer's protocol, and cells are incubated for three hours in the presence of reagent before O.D. reading is done. Compounds were diluted to final concentrations of 0, 5, 10, 20, and 50 µM in media containing 0.5% DMSO. Negative control wells contain no compound and positive control for cytotoxicity is examined using an EMCV infection which causes 100% cytopathic effect. Each compound concentration and control is done in triplicate wells to generate error bars.

EMCV antiviral assay. Cultured human Huh7 cells are seeded at $1.5 \times 10^4$ cells/well and are pretreated with compound or equivalent amounts of media containing DMSO (negative control) for 24 hours. Then each well is infected with 250 pfu EMCV and incubated for 18 hours under normal growth conditions. Positive control wells are treated with 50 IU/mL Intron A. The level of viable cells is calculated using a cell viability assay that measures conversion of a tetrazolium compound [3-(4,5-dimethyl-2-yl)-5-(3-carboxymethoxyphenyl)-2-(4-sulfophenyl)-2H-tetrazolium, inner salt; MTS] to a colored formazan compound in live cells. The conversion of MTS to formazan is detected in a 96-well microtiter plate reader, and the resulting optical densities can be plotted directly to estimate cell viability. Cell Titer One is used as described above.

HCV IF antiviral assay. Huh7 cells are seeded on a 96 well plate at $5 \times 10^3$ cells per well and cells are allowed to attach and grow for 24 hours. Compounds that have been diluted to 10 µM in media and contain a final concentration of 0.5% DMSO are added to each well and grown another 24 hours. The compound media solution is removed from the plate and stored in a clean tissue culture dish. Cell monolayers are washed with PBS and HCV2a virus is added at the stated multiplicity of infections (MOI). Virus is incubated for 2-4 hours and then removed, the monolayers are washed with PBS and the compound solutions are replaced into each well.

The cells are grown overnight and then cells are fixed and stained for HCV proteins. All buffers and reagents are used from the Cellomics staining kits described above. Primary serum PHS#72 is diluted 1:3,000 in wash buffer and incubated at room temperature 1 hour. The secondary anti-human Dylight 488 or FITC Alexa 488 and Hoescht nuclear stain are diluted as stated in protocol. Cells are washed and 100 µl of wash buffer is left in each well. Cellular staining is observed on an inverted microscope and images are taken as described above. The number of infected cells is counted and representative images are saved.

Influenza A virus ELISA assay. A549 cells are seeded in a 96 well plate; $1 \times 10^4$ cells/well. Cells are grown for 16 hours and compounds that were diluted to 5, 10, 20, 50 µM in media containing 0.5% DMSO are added to each well. Cells are incubated for 6 hours and then infected with 250 pfu Influenza WSN strain. Diluted virus is added directly to the well and compound is not removed. Infected cells are grown for a total of 24 hours post compound treatment and then fixed. The WSN Influenza ELISA protocol is done as follows: Cells are washed with PBS, fixed with methanol:acetone for 10 minutes and washed again with PBS.

Cells are blocked with Horse serum and BSA in the presence of Triton X-100. The primary antibody used at a 1:3000 dilution is Mouse anti-Influenza A Nucleoprotein Monoclonal (Chemicon). The secondary antibody used is Goat anti-mouse IgG-HRP (Pierce) and this is diluted 1:3000 as well. The reaction is developed using TMBK BioFX reagents as suggested. Following reagent addition the cells are incubated at room temperature for 2-5 minutes and 2N HCl is used to stop the reaction. Plates are read at 450 nM.

Final KIN600 concentrations of 50 µM, 20 µM, 10 µM, and 5 µM were made in 0.5% DMSO containing media and were added to Huh7 cells to examine cytotoxicity in a MTS assay. Cells were treated for 24 hours with varying concentrations of compound and were analyzed for cell viability compared to negative control samples that were not treated with compound but grown in DMSO containing media. The cellular metabolism (O.D.) was in the range of 1.75 to below 2.0 at compound concentrations of 50 µM, 20 µM, 10 µM, 5 µM, and 0. KIN600 was confirmed to have no significant toxicity.

Antiviral characterization. KIN600 compounds are initially examined for antiviral activity against Influenza A virus-WSN strain (IFA) using an ELISA method to detect levels of infection. KIN600 compounds are also examined for antiviral activity against Hepatitis C virus. To analyze antiviral activity cells were pre-treated with compound at 10 µM and subsequently infected with HCV2a purified virus. HCV2a was synthesized from a constructed clone, amplified in Huh7 cells and concentrated to obtain high viral titers. The virus used in these experiments was approximately $5 \times 10^5$ pfu/mL and the antiviral experiments used an MOI of 0.1-0.5.

To measure levels of HCV infection with or without drug treatment, the cells were stained for HCV specific staining using serum and a FITC conjugated fluorescent secondary antibody. HCV protein staining is specific, showed low background in mock infected cells and stained only the cytoplasm of cells where HCV replication occurs. Using an inverted fluorescent microscope the number of infected cells was quantitated. Interferon treatment was used as a positive control and completely blocks HCV infection. A negative control compound that did not cause IRF-3 translocation was used to show that the antiviral activity is not due to treatment with any small molecule. For the negative control, the HCV infected foci (number of FFU/well) was 35±11, and for KIN600, the HCV infected foci (number of FFU/well) was 12±4. In summary, Huh7 cells were pre-treated with KIN600 for 24 hours, infected with HCV at a low MOI for 48 hours and then stained for HCV proteins. Mock infected cells showed no background staining, and interferon completely blocked infection and serves as a positive control. The number of infected cells were counted on an inverted microscope.

Antiviral activity for HCV infection is examined following treatment with increasing concentrations of KIN600 compounds. Additionally, KIN600 compounds are analyzed for antiviral activity against HCV with increasing MOI of virus added. For example, Huh7 cells are pre-treated with KIN600 compound at increasing concentrations 0-10 µM for 24 hours. Cells are then infected and analyzed for HCV foci as described above. For increasing MOI of virus, Huh7 cells are treated with 10 µM of compound for 24 hours and subsequently HCV infections at, for example, 0.25, 0.5 and 2 MOI, are performed as described above.

In conclusion, this Example shows that KIN600 has antiviral properties.

Example 2

EMCV Antiviral Assay

Huh7 cells were grown under normal growth conditions and treated with the indicated amount of drug in media containing 0.5% DMSO. The cells were grown in the presence of drug for 5 hours and then infected with 250 pfu Murine Encephalomyocarditis virus (EMCV) for example obtained from ATCC #VR-129B. Infected cells were grown for an additional 18 hours and then cell viability was measured using an MTS assay. Negative control cells were treated with buffer alone containing 0.5% DMSO. Interferon treatment was used as a positive control for virus inhibition and was added similar to drug treatments at a final concentration of 10 IU/mL for example Interferon-α: Intron A, from Schering-Plough. Cell viability was measured using an MTS assay such as; CellTiter 96® AQueous One Solution Cell Proliferation Assay (MTS), from Promega #G3580.

Figure 1B:
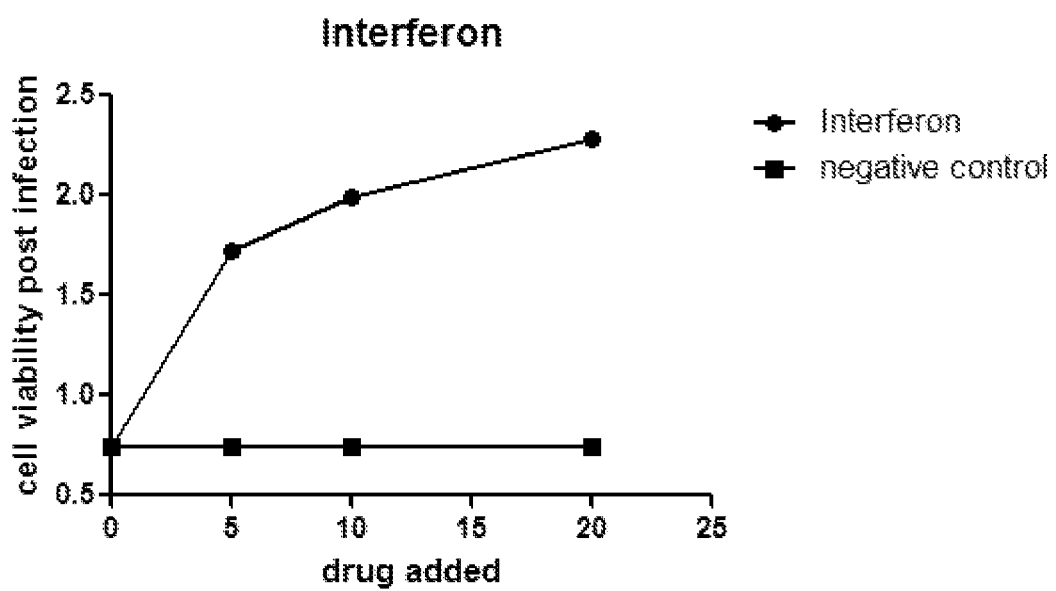

Results are shown in FIGS. 1A and 1B and are as described below:

| Addition (drug or control) | Cell viability post-infection |
|---|---|
| Negative controls | ~0.7-0.75 |
| 5 IU/ml interferon | ~1.7 |
| 10 IU/ml interferon | ~2.0 |
| 20 IU/ml interferon | ~2.25 |
| 5 µL KIN 600 | ~0.7 |
| 10 µL KIN 600 | ~1.4 |

Example 3

Antiviral Activity and Pharmacological Properties Using Quantitative Structure-Activity Relationship (QSAR) Studies This Example describes optimization of KIN600 compounds for antiviral action. For optimization, a two-stage QSAR approach is used; starting with a small analog derivative set to define structural class followed by derivative expansion. Active analogs identified in the first stage will be used to define a subset of structural classes of interest for further optimization in stage 2.

Stage 2 will focus on creating structural diversity and evaluating core variants. Structural derivatives will be tested for biological activity in antiviral activity against HCV and influenza virus, and cytotoxicity in one or more cell lines or peripheral blood mononuclear cells. Optimized molecules that show improved efficacy and low cytotoxicity will be further characterized by additional measures of in vitro toxicology and absorption, distribution, metabolism, and elimination (ADME). Their mechanism of action and breadth of antiviral activity will also be studied.

Chemical design in QSAR studies. To design analog structures, we will analyze drug-like properties, metabolic lability, and toxic potential of the lead compounds. Drug-like properties, as measured by Lipinski's Rules (18), and related physiochemical properties are primary indicators of bioavailability. Structural features that suggest metabolic and toxicological liabilities may indicate limited stability, reduced half-life, reactive intermediates, or idiosyncratic toxicity and will therefore be removed. A 5- to 10-compound analog set is constructed to remove or alter chemically reactive or metabolically susceptible structural features, thereby developing a preliminary QSAR.

KIN600 compounds are tested for in vitro antiviral activity against HCV 2A and influenza A virus (A/WSN/33). Viral protein and RNA levels are assessed following drug treatment using the assays described above.

Following several iterative rounds of QSAR, KIN600 compounds are selected for characterization of their in vitro toxicological and ADMA properties and for further mechanistic study. The QSAR studies are designed to provide lead compounds with picomolar to nanomolar potency, which is adequate to support preclinical development.

In vitro pharmacology. In vitro pharmacology studies are performed to measure performance of the most promising analogs in one or more assays of intestinal permeability, metabolic stability and toxicity. Key in vitro characterization studies can include plasma protein binding; serum, plasma, and whole-blood stability in human and model organisms; intestinal permeability; intrinsic clearance; human Ether-à-go-go (hERG) channel inhibition; and genotoxicity.

For each analog, an HPLC- and/or HPLC-mass spectrometry-based analytical method will be used to evaluate drug and metabolite concentrations in various test systems. Although the specific analytical method is optimized for each molecule, reverse-phase chromatography can be used alone or in combination with quadrupole mass spectrometry to characterize the identity and purity of several of the lead molecules. Initially, drug stability over time in increasing concentrations of serum, plasma, and whole blood from mammalian species (such as mouse, cynomolgus macaque, and human) will be evaluated by HPLC, and a half-life will be determined.

In some instances, prominent metabolites are characterized by mass spectrometry. Human plasma protein binding will be evaluated by partition analysis using equilibrium dialysis. For intestinal permeability modeling, apical-to-basolateral flux is assessed in the human epithelial cell line TC7. Hepatic clearance is estimated for a subset of the most promising analogs by measuring the rate of disappearance of the parent compound during incubation in human liver microsomes. As above, specific metabolites may be isolated and characterized.

In vitro toxicology. This description of toxicological assays is exemplary and not intended to be limiting. In vitro toxicology studies are performed to evaluate the potential cardiac and genetic toxicity of lead analogs. Automated patch-clamp can be used to assess the impact of each compound on hERG channel currents in a recombinant Chinese hamster ovary (CHO) cell line transgenically expressing the human Kv11.1 gene. Concentrations up to the lesser of 30 times the maximum serum concentration or the limit of solubility of each compound are evaluated in order to determine an IC50 for the molecule on the hERG channel. A subset of compounds is evaluated over a range of concentrations for their ability to induce mutation reversion in *Salmonella typhimurium* strains TA98 and TA100 or to promote micronucleus formation in CHO cells in culture.

Example 4

Antiviral Activity OF KIN600 Compounds

Antiviral action in cell culture infection models. KIN600 compounds disclosed herein have efficient activity against HCV genotype 2a and influenza virus strain WSN. To further characterize the breadth of antiviral activity of optimized molecules, cell culture infection models are used to analyze different HCV genotypes and influenza virus strains. In addition, optimized compounds are tested for activity against West Nile virus (WNV), an emerging public health concern. The studies include treating cells with compound 2-12 h prior to infection or treating cells 8 h after infection (Table 2). Virus production and cellular ISG expression are assessed over a time course to analyze antiviral effects of representative compounds from lead structural classes. IFNβ treatment is used as a positive control.

Virus production is measured by focus-forming or plaque assay. In parallel experiments, viral RNA and cellular ISG expression are measured by qPCR and immunoblot analyses. These experiments are designed to validate compound signaling actions during virus infection, and assess compound actions to direct innate immune antiviral programs against various strains of viruses and in the setting of virus countermeasures. Detailed dose-response analyses of each compound are conducted in each virus infection system to determine the effective dose that suppresses virus production by 50% (IC50) and 90% (IC90) as compared with control cells for both the pre-treatment and post-treatment infection models.

TABLE 2

Virus systems and study design for antiviral analysis of lead compounds

| Virus | Virus Strain | Study Design |
|---|---|---|
| HCV | H77 (genotype 1a) | Assays |
|  | JFH1 (genotype 2a) | Plaque or focus forming |
| FLU | High pathogenicity in mice | assays |
|  | A/PR/8/34 (H1N1 mouse-adapted virus) | (infectious virus) |
|  | A/WSN/33 (H1N1 mouse-adapted neurovirulent virus) | qPCR (RNA levels) Immunoblot and ELISA (protein levels) |
|  | Low pathogenicity in mice | Study Design |
|  | A/Texas/36/91 (H1N1 circulating virus) | Compound treatment of cells pre- and post-infection |
|  | A/Udorn/72 (H3N2) | Determine $EC_{50}$ and $EC_{90}$ |
| WNV | TX02 (lineage 1) | Inhibition of viral |
|  | MAD78 (lineage 2) | life cycle |

Example 5

In Vivo Pharmacokinetic, Toxicological, and Antiviral Properties of Optimized Drug Leads in Relevant Preclinical Animal Models Preclinical pharmacokinetic and tolerability profiling. The in vivo pharmacokinetic (PK) profile and tolerability/toxicity of KIN600 compounds are evaluated in order to conduct further characterization of their antiviral activity in animal models of influenza virus and WNV infection. Mouse is the chosen test species for these studies since it is the most commonly used rodent model of WNV and influenza.

A reverse-phase, HPLC-MS/MS detection method is used for measuring the concentration of each compound in mouse plasma. Prior to PK profiling, an initial oral and intravenous formulation for each compound is developed using a limited formulation component screen that is largely focused on maximizing aqueous solubility and stability over a small number of storage conditions. Existing analytical methods known in the art are used to measure formulation performance. A formulation is developed for each compound following a three tiered strategy:

Tier 1: pH (pH 3 to 9), buffer, and osmolality adjustment

Tier 2: addition of ethanol (<10%), propylene glycol (<40%), or polyethylene glycol (PEG) 300 or 400 (<60%) co-solvents to enhance solubility Tier 3: addition of N—N-dimethylacetamide (DMA, <30%), N-methyl-2-pyrrolidone (NMP, <20%), and/or dimethyl sulfoxide (DMSO, <20%) co-solvents or the cyclodextrins (<40%) as needed to further improve solubility.

For compounds that demonstrate adequate performance in in vitro antiviral, mechanistic, ADME, and toxicology studies, a preliminary mouse PK study is performed (Table 3). Each compound is administered as a single dose to animals by oral gavage (<10 ml/kg) or i.v. bolus injection (<5 ml/kg) after an overnight fast. Multiple animals are dosed for each dosing group such that 3 animals can be sampled at each time point. Blood samples are collected by retro-orbital sinus prior to dosing and at 5, 15, and 30 min, and 1, 2, 4, 8, and 24 h post dosing. Drug concentrations are measured according to the previously developed bioanalytical method. Pharmacokinetic parameters are evaluated using the WinNonlin software.

TABLE 3

| Study | Experimental design | Route of administration | Outcomes |
|---|---|---|---|
| Mouse PK | Single dose pharmacokinetic study | IV and Oral | Oral bioavailability, $C_{max}$, $t_{1/2}$, Cl, $V_d$, $AUC_{0-24, 0-\infty}$ |
| Mouse tolerability | Phase 1: ascending dose tolerability and MTD determination; Phase 2: placebo controlled 7-day toxicity at MTD | Oral | MTD, acute toxicity, hematology, serum chemistry, gross pathology |

Based upon performance in exploratory PK studies, compounds are further evaluated for preliminary tolerability and toxicity in mice prior to their characterization in antiviral models. Tolerability studies are performed in two stages: an initial dose escalation stage (up to 5 doses, each separated by a 5-day washout period) to determine the maximum tolerable dose (MTD, Phase 1), followed by seven daily administrations of the MTD to evaluate acute toxicity (Stage 2) (Table 4). All doses are administered by oral gavage. In an exemplary experiment, five animals of each sex are placed on-study in stage 1 and 15 animals per sex per dosing group in Stage 2. Study endpoints include a determination of the MTD, physical examination, clinical observations, hematology, serum chemistry and animal bodyweights. Gross pathology is performed on all animals whether found dead, euthanized in extrimis, or at the intended conclusion of the experiment. The toxicology studies are primarily exploratory in nature and intended to identify early toxicological endpoints, and drive selection of lead candidates for antiviral animal models.

TABLE 4

In vivo studies of compound actions against WNV and influenza virus

| Experiment | Analysis | Goal | Exemplary No. of Mice* |
|---|---|---|---|
| Effective compound dose determination | Viral burden analysis in serum | Define in vivo $EC_{50}$ and $EC_{90}$ | 238 |
| Viral pathogenesis study 1: $EC_{50}$ and $EC_{90}$ treatment | Time to moribund state, clinical scoring for pathologic signs of infection | Define compound action toward limiting viral pathogenesis | 739 |
| Viral pathogenesis study 2: $EC_{50}$ and $EC_{90}$ treatment and time course analysis | Viral burden analysis in serum and various target organs | Define compound action toward limiting virus replication and spread | 1056 |
| Viral pathogenesis study 3: (neuroinvasion model) $EC_{50}$ and $EC_{90}$ treatment | Time to moribund state, clinical scoring for pathologic signs of infection | Define compound action toward limiting viral pathogenesis in the CNS | 370 |

*Numbers reflect an average of at least two iterations of each experiment

Evaluation of antiviral properties and immune protection using mouse infection models. Optimized compounds are selected based on compound pharmacokinetic, antiviral, and innate immune actions for further evaluation in preclinical mouse models of infection (Table 4). Innate immune actions of the compounds are measured, and their ability to protect mice from WNV and influenza virus challenge is assessed. For the WNV infection model, subcutaneous footpad infection of wild-type C57Bl/6 mice with the virulent lineage 1 strain of WNV (WNV-TX) are performed (29). Non-surgical tracheal instillation is performed for influenza virus strains A/PR/8/34, A/WSN/33, and A/Udorn/72.

The influenza virus strains used for certain experiments are of two different subtypes (H1N1 and H3N2) and exhibit varying pathogenic properties and clinical presentations in C57Bl/6 mice (30). Mice are monitored for morbidity and mortality over a range of challenge doses (such as, 10 to 1,000 pfu of virus) either alone or in combination with compound treatment beginning 12 h before or 24 h after infection and continuing daily subject to the determined plasma half-life of the drug. Compound dose-response analysis and infection time course studies are conducted to evaluate compound efficacy to: 1) limit serum viral load, 2) limit virus replication and spread in target organs, and 3) protect against viral pathogenesis.

For WNV, in addition to serum, viral burden is assessed in lymph nodes, spleen, and brain; for influenza virus, viral burden is assessed in heart, lung, kidney, liver, and brain. Incorporated in the design of these experiments is the determination of an effective dose for 50% and 90% suppression of serum viral load (ED50 and ED90) by each compound after a standard challenge of 100 pfu of WNV-TX or 1,000 pfu of influenza virus. Serum viral loads are determined by qPCR of viral RNA at 24 h intervals following compound treatment. The compound actions are tested at the ED50 and ED90 toward limiting WNV pathogenesis in the cerebral nervous system using a WNV neuroinvasion model of infection (31).

Mice are monitored for morbidity and mortality after standard intracranial challenge of 1 pfu of WNV-MAD, either alone or in combination with compound treatment beginning 24 h after infection.

Example 6

Methyl 3-(1,3-benzodioxol-5-ylsulfamoyl)thiophene-2-carboxylate

To a solution of amine 2 (17.7 mmol) in anhydrous THF (60 ml) at 0° C. is added NaH (60% dispersion in mineral oil, 37.4 mmol). The resulting mixture is stirred for 10 min before the slow addition of sulfonyl chloride 1(12.5 mmol). The reaction mixture is stirred at room temperature for 4 h. To work up, the mixture is diluted with hexanes (60 ml) and the resulting precipitate is filtered and washed with hexanes, to give compound 3 (76% yield).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

In closing, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

REFERENCES

1. Tan, S. L., Ganji, G., Paeper, B., Proll, S., and Katze, M. G. (2007) Systems biology and the host response to viral infection, *Nat Biotechnol* 25, 1383-1389.
2. Lee, J., Wu, C. C., Lee, K. J., Chuang, T. H., Katakura, K., Liu, Y. T., Chan, M., Tawatao, R., Chung, M., Shen, C., Cottam, H. B., Lai, M. M., Raz, E., and Carson, D. A. (2006) Activation of anti-hepatitis C virus responses via Toll-like receptor 7, *Proc Natl Acad Sci USA* 103, 1828-1833.
3. Horsmans, Y., Berg, T., Desager, J. P., Mueller, T., Schott, E., Fletcher, S. P., Steffy, K. R., Bauman, L. A., Kerr, B. M., and Averett, D. R. (2005) Isatoribine, an agonist of TLR7, reduces plasma virus concentration in chronic hepatitis C infection, *Hepatology* 42, 724-731.
4. Johnson, C. L., and Gale, M., Jr. (2006) CARD games between virus and host get a new player, *Trends Immunol* 27, 1-4.
5. Li, K., Chen, Z., Kato, N., Gale, M., Jr., and Lemon, S. M. (2005) Distinct poly(1-C) and virus-activated signaling pathways leading to interferon-beta production in hepatocytes, *J Biol Chem* 280, 16739-16747.
6. Loo, Y. M., Fornek, J., Crochet, N., Bajwa, G., Perwitasari, O., Martinez-Sobrido, L., Akira, S., Gill, M. A., Garcia-Sastre, A., Katze, M. G., and Gale, M., Jr. (2008) Distinct RIG-I and MDA5 signaling by RNA viruses in innate immunity, *J Virol* 82, 335-345.
7. Loo, Y. M., Owen, D. M., Li, K., Erickson, A. K., Johnson, C. L., Fish, P. M., Carney, D. S., Wang, T., Ishida, H., Yoneyama, M., Fujita, T., Saito, T., Lee, W. M., Hagedorn, C. H., Lau, D. T., Weinman, S. A., Lemon, S. M., and Gale, M., Jr. (2006) Viral and therapeutic control of IFN-beta promoter stimulator 1 during hepatitis C virus infection, *Proc Natl Acad Sci USA* 103, 6001-6006.
8. Saito, T., Hirai, R., Loo, Y. M., Owen, D., Johnson, C. L., Sinha, S. C., Akira, S., Fujita, T., and Gale, M., Jr. (2007) Regulation of innate antiviral defenses through a shared repressor domain in RIG-I and LGP2, *Proc Natl Acad Sci USA* 104, 582-587.
9. Saito, T., Owen, D. M., Jiang, F., Marcotrigiano, J., and Gale, M., Jr. (2008) Innate immunity induced by composition-dependent RIG-I recognition of hepatitis C virus RNA, *Nature* 454, 523-527.
10. Sumpter, R., Jr., Loo, Y. M., Foy, E., Li, K., Yoneyama, M., Fujita, T., Lemon, S. M., and Gale, M., Jr. (2005) Regulating intracellular antiviral defense and permissiveness to hepatitis C virus RNA replication through a cellular RNA helicase, RIG-I, *J Virol* 79, 2689-2699.
11. Yoneyama, M., Kikuchi, M., Natsukawa, T., Shinobu, N., Imaizumi, T., Miyagishi, M., Taira, K., Akira, S., and Fujita, T. (2004) The RNA helicase RIG-I has an essential function in double-stranded RNA-induced innate antiviral responses, *Nat Immunol* 5, 730-737.
12. Kawai, T., Takahashi, K., Sato, S., Coban, C., Kumar, H., Kato, H., Ishii, K. J., Takeuchi, O., and Akira, S. (2005) IPS-1, an adaptor triggering RIG-1- and Mda5-mediated type I interferon induction, *Nat Immunol* 6, 981-988.
13. Meylan, E., Curran, J., Hofmann, K., Moradpour, D., Binder, M., Bartenschlager, R., and Tschopp, J. (2005) Cardif is an adaptor protein in the RIG-I antiviral pathway and is targeted by hepatitis C virus, *Nature* 437, 1167-1172.
14. Seth, R. B., Sun, L., Ea, C. K., and Chen, Z. J. (2005) Identification and characterization of MAVS, a mitochondrial antiviral signaling protein that activates NF-kappaB and IRF 3, *Cell* 122, 669-682.
15. Xu, L. G., Wang, Y. Y., Han, K. J., Li, L. Y., Zhai, Z., and Shu, H. B. (2005) VISA is an adapter protein required for virus-triggered IFN-beta signaling, *Mol Cell* 19, 727-740.
16. Venkataraman, T., Valdes, M., Elsby, R., Kakuta, S., Caceres, G., Saijo, S., Iwakura, Y., and Barber, G. N. (2007) Loss of DExD/H box RNA helicase LGP2 manifests disparate antiviral responses, *J Immunol* 178, 6444-6455.
17. Lipinski, C. A., Lombardo, F., Dominy, B. W., and Feeney, P. J. (2001) Experimental and computational approaches to estimate solubility and permeability in drug discovery and development settings, *Adv Drug Deliv Rev* 46, 3-26.
18. Banerjee, S., Li, Y., Wang, Z., and Sarkar, F. H. (2008) Multi-targeted therapy of cancer by genistein, *Cancer Lett* 269, 226-242.
19. Odaka, M., Kohda, D., Lax, I., Schlessinger, J., and Inagaki, F. (1997) Ligand-binding enhances the affinity of dimerization of the extracellular domain of the epidermal growth factor receptor, *J Biochem* 122, 116-121.
20. Philo, J. S., Wen, J., Wypych, J., Schwartz, M. G., Mendiaz, E. A., and Langley, K. E. (1996) Human stem cell factor dimer forms a complex with two molecules of the extracellular domain of its receptor, Kit, *J Biol Chem* 271, 6895-6902.
21. Philo, J. S., Aoki, K. H., Arakawa, T., Narhi, L. O., and Wen, J. (1996) Dimerization of the extracellular domain of the erythropoietin (EPO) receptor by EPO: one high-affinity and one low-affinity interaction, *Biochemistry* 35, 1681-1691.
22. Kato, H., Takeuchi, O., Sato, S., Yoneyama, M., Yamamoto, M., Matsui, K., Uematsu, S., Jung, A., Kawai, T., Ishii, K. J., Yamaguchi, O., Otsu, K., Tsujimura, T., Koh, C. S., Reis e Sousa, C., Matsuura, Y., Fujita, T., and Akira, S. (2006) Differential roles of MDA5 and RIG-I helicases in the recognition of RNA viruses, *Nature* 441, 101-105.
23. Yoneyama, M., Kikuchi, M., Matsumoto, K., Imaizumi, T., Miyagishi, M., Taira, K., Foy, E., Loo, Y. M., Gale, M., Jr., Akira, S., Yonehara, S., Kato, A., and Fujita, T. (2005) Shared and unique functions of the DExD/H-box helicases RIG-I, MDA5, and LGP2 in antiviral innate immunity, *J Immunol* 175, 2851-2858.
24. Lescuyer, P., Strub, J. M., Luche, S., Diemer, H., Martinez, P., Van Dorsselaer, A., Lunardi, J., and Rabilloud, T. (2003) Progress in the definition of a reference human mitochondrial proteome, *Proteomics* 3, 157-167.
25. Taylor, S. W., Fahy, E., Zhang, B., Glenn, G. M., Warnock, D. E., Wiley, S., Murphy, A. N., Gaucher, S. P., Capaldi, R. A., Gibson, B. W., and Ghosh, S. S. (2003) Characterization of the human heart mitochondrial proteome, *Nat Biotechnol* 21, 281-286.
26. Lutfalla, G., Holland, S. J., Cinato, E., Monneron, D., Reboul, J., Rogers, N. C., Smith, J. M., Stark, G. R., Gardiner, K., Mogensen, K. E., and et al. (1995) Mutant U5A cells are complemented by an interferon-alpha beta receptor subunit generated by alternative processing of a new member of a cytokine receptor gene cluster, *EMBO J.* 14, 5100-5108.
27. Zou, J., Chang, M., Nie, P., and Secombes, C. J. (2009) Origin and evolution of the RIG-I like RNA helicase gene family, *BMC Evol Biol* 9, 85.
28. Renard, P., Ernest, I., Houbion, A., Art, M., Le Calvez, H., Raes, M., and Remacle, J. (2001) Development of a sensitive multi-well colorimetric assay for active NFkappaB, *Nucleic Acids Res* 29, E21.
29. Suthar, M. S., Ma, D. Y., Thomas, S., Lund, J. M., Zhang, N., Daffis, S., Rudensky, A. Y., Bevan, M. J., Clark, E. A., Kaja, M. K., Diamond, M. S., and Gale, M., Jr. (2010) IPS-1 is essential for the control of West Nile virus infection and immunity, *PLoS Pathog* 6, e1000757.
30. Barnard, D. L. (2009) Animal models for the study of influenza pathogenesis and therapy, *Antiviral Res* 82, A110-122.
31. Daffis, S., Samuel, M. A., Suthar, M. S., Gale, M., Jr., and Diamond, M. S. (2008) Toll-like receptor 3 has a protective role against West Nile virus infection, *J Virol* 82, 10349-10358.
32. Blight, J. J. et al., (2002) J. Virology 76:13001-13014.

We claim:

1. A pharmaceutical composition comprising a compound or a salt, tautomer and/or isomer thereof having a structure:

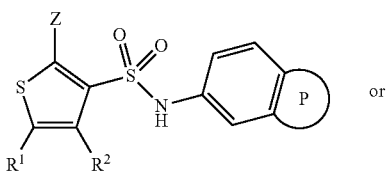

or

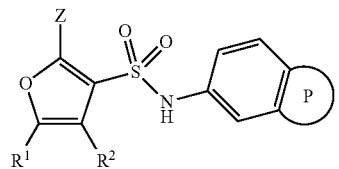

wherein $R^1$ and $R^2$ are each independently selected from H, lower alkyl, aryl, alkenyl, alkynyl, alkylaryl, arylalkyl, alkoxy, aryloxy, arylalkoxy, alkoxyalkylaryl, alkylamino, aminoalkyl, dialkylamino, arylamino, aminoaryl, heteroalkyl, heteroaryl, heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazole, thiazole, isothiazole, imidazole, thiadiazole, thiadiazole S-oxide, thiadiazole S,S-dioxide, sulfonylamidine, sulfonylguanidine, sulfamoylamidine, sulfamoylguanidine, pyrazole, oxazole, isoxazole, pyridinyl, pyrimidinyl, piperazine, quinoline, isoquinoline, $SR^5$, $SOR^5$, $SO_2R^5$, $CO_2R^5$, $COR^5$, $CONR^5R^6$, $CSNR^5R^6$, $SO_mNR^5R^6$ or when $R^1$ and $R^2$ taken together form cyclic methylene dioxo, benzo, morpholino, piperidinyl, dioxanyl, pyranyl, heteroaryl, furanyl, thiophene, pyrrole, thiazole, isothiazole, imidazole, oxazole, isoxazole, pyridinyl, pyrimidinyl or piperazine;

Z is selected from H, lower alkyl, aryl, alkenyl, alkynyl, alkylaryl, arylalkyl, alkoxy, aryloxy, arylalkoxy, alkoxyalkylaryl, alkylamino, aminoalkyl, dialkylamino, arylamino, aminoaryl, heteroalkyl, heteroaryl, heteroarylalkyl, cyclic heteroalkyl, cyclic heteroalkylalkyl, acyl, $NH_2$, $NR^5R^6$, OH, $OR^5$, CN, $NO_2$, $OCF_3$, $CF_3$, Br, Cl, F, 1-amidino, 2-amidino, alkylcarbonyl, morpholino, piperidinyl, dioxanyl, pyranyl, heteroaryl, furanyl, thiophenyl, tetrazole, thiazole, isothiazole, imidazole, thiadiazole, thiadiazole S-oxide, thiadiazole S,S-dioxide, sulfonylamidine, sulfonylguanidine, sulfamoylamidine, sulfamoylguanidine, pyrazole, oxazole, isoxazole, pyridinyl, pyrimidinyl, piperazine, quinoline, isoquinoline, $SR^5$, $SOR^5$, $SO_2R^5$, $CO_2R^5$, $COR^5$, $CONR^5R^6$, $CSNR^5R^6$, or $SO_mNR^5R^6$;

$R^5$ and $R^6$ are each independently selected from H, lower alkyl, aryl, alkenyl, alkynyl, alkylaryl, arylalkyl, alkoxy, aryloxy, arylalkoxy, heteroalkyl, heteroaryl, heteroarylalkyl, cyclic heteroalkyl or cyclic heteroalkylalkyl; and wherein ring P is a substituted or non-substituted methylene dioxo, benzo, morpholino, piperidinyl, dioxanyl, pyranyl, heteroaryl, furanyl, thiophene, pyrrole, thiazole, isothiazole, imidazole, oxzole, isoxazole, pyridinyl, pyrimidinyl or piperazine.

2. A pharmaceutical composition of claim 1 wherein the compound has a formula:

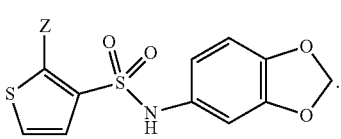

3. A pharmaceutical composition of claim 1 wherein the compound has a formula:

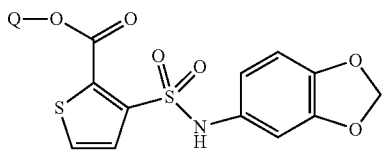

wherein Q is H or lower alkyl.

4. A pharmaceutical composition of claim 1 wherein the compound has a formula:

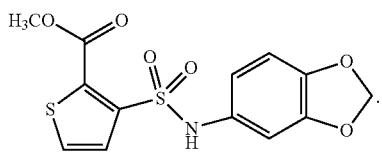 [SMILES: COC(=O)c1sccc1S(=O)(=O)Nc1ccc2c(c1)OCO2]

5. A method of treating a viral infection in a vertebrate comprising administering a pharmaceutical composition of claim 1 wherein the compound modulates the RIG-I pathway.

6. A method of claim 5 wherein the viral infection is caused by a virus from one of the following families: Arenaviridae, Astroviridae, Birnaviridae, Bromoviridae, Bunyaviridae, Caliciviridae, Closteroviridae, Comoviridae, Cystoviridae, Flaviviridae, Flexiviridae, Hepevirus, Leviviridae, Luteoviridae, Mononegavirales, Mosaic Viruses, Nidovirales, Nodaviridae, Orthomyxoviridae, Picobirnavirus, Picornaviridae, Potyviridae, Reoviridae, Retroviridae, Sequiviridae, Tenuivirus, Togaviridae, Tombusviridae, Totiviridae, Tymoviridae, Hepadnaviridae, Herpesviridae, Paramyxoviridae or Papillomaviridae.

7. A method of claim 5 wherein the viral infection is caused by influenza virus, Hepatitis C virus, West Nile virus, SARS-coronavirus, poliovirus, measles virus, Dengue virus, yellow fever virus, tick-borne encephalitis virus, Japanese encephalitis virus, St. Louis encephalitis virus, Murray Valley virus, Powassan virus, Rocio virus, louping-ill virus, Banzi virus, Ilheus virus, Kokobera virus, Kunjin virus, Alfuy virus, bovine diarrhea virus, Kyasanur forest disease virus and/or human immunodeficiency virus (HIV).

* * * * *